(12) United States Patent
Ramanathan et al.

(10) Patent No.: US 11,576,604 B2
(45) Date of Patent: Feb. 14, 2023

(54) SYSTEMS AND METHODS FOR ASSESSING HEART FUNCTION

(71) Applicant: CARDIOINSIGHT TECHNOLOGIES, INC., Independence, OH (US)

(72) Inventors: Charulatha Ramanathan, Solon, OH (US); Harold Wodlinger, Thornhill (CA); Maria Strom, Moreland Hills, OH (US); Steven G. Arless, Baie Durfe (CA); Ping Jia, Solon, OH (US)

(73) Assignee: CARDIOINSIGHT TECHNOLOGIES INC., Independence, OH (US)

( * ) Notice: Subject to any disclaimer, the term of this patent is extended or adjusted under 35 U.S.C. 154(b) by 328 days.

(21) Appl. No.: 16/870,134

(22) Filed: May 8, 2020

(65) Prior Publication Data
US 2020/0260978 A1    Aug. 20, 2020

Related U.S. Application Data

(63) Continuation of application No. 15/805,903, filed on Nov. 7, 2017, now Pat. No. 10,682,066, which is a
(Continued)

(51) Int. Cl.
*A61B 5/00* (2006.01)
*A61N 1/362* (2006.01)
(Continued)

(52) U.S. Cl.
CPC ............ *A61B 5/316* (2021.01); *A61B 5/0036* (2018.08); *A61B 5/0044* (2013.01);
(Continued)

(58) Field of Classification Search
CPC .............. A61B 5/0044; A61B 5/02028; A61B 5/6801
See application file for complete search history.

(56) References Cited

U.S. PATENT DOCUMENTS 6,301,496 B1   10/2001   Reisfeld
6,622,040 B2    9/2003   Ding
(Continued)

FOREIGN PATENT DOCUMENTS

EP        20116976 A1    1/2009
WO       2004045710      6/2004
(Continued)

OTHER PUBLICATIONS

Jennifer Silva, M.D, "Cardiac Resynchronization Therapy in Pediatric Congenital Heart Disease: Insights From Noninvasive Electrocardiographic Imaging", Heart Rhythm Society, Apr. 17, 2009, 8 pgs.
(Continued)

*Primary Examiner* — Michael W Kahelin
(74) *Attorney, Agent, or Firm* — Tarolli, Sundheim, Covell & Tummino LLP

(57) ABSTRACT

Systems and methods can be used to provide an indication of heart function, such as an indication of mechanical function or hemodynamics of the heart, based on electrical data. For example, a method for assessing a function of the heart can include determining a time-based electrical characteristic for a plurality of points distributed across a spatial region of the heart. The plurality of points can be grouped into at least two subsets of points based on at least one of a spatial location for the plurality of points or the time-based electrical characteristics for the plurality of points. An indication of synchrony for the heart can be quantified based on relative analysis of the determined time-based electrical characteristic for each of the at least two subsets of points.

20 Claims, 12 Drawing Sheets

Related U.S. Application Data continuation of application No. 14/798,124, filed on Jul. 13, 2015, now Pat. No. 9,826,915, which is a continuation of application No. 13/882,912, filed as application No. PCT/US2011/059174 on Nov. 3, 2011, now Pat. No. 9,078,573.

(60) Provisional application No. 61/409,714, filed on Nov. 3, 2010.

(51) Int. Cl.

| | |
|---|---|
| A61B 5/02 | (2006.01) |
| A61B 5/316 | (2021.01) |
| A61B 5/11 | (2006.01) |
| A61B 5/318 | (2021.01) |
| A61B 5/349 | (2021.01) |
| A61N 1/368 | (2006.01) |
| A61B 5/283 | (2021.01) |
| A61B 5/287 | (2021.01) |

(52) U.S. Cl.
CPC ........ *A61B 5/02028* (2013.01); *A61B 5/1107* (2013.01); *A61B 5/318* (2021.01); *A61B 5/349* (2021.01); *A61B 5/4848* (2013.01); *A61B 5/6801* (2013.01); *A61N 1/362* (2013.01); *A61B 5/283* (2021.01); *A61B 5/287* (2021.01); *A61N 1/368* (2013.01); *A61N 1/3627* (2013.01)

(56) References Cited

U.S. PATENT DOCUMENTS

| | | | |
|---|---|---|---|
| 7,013,176 | B2 | 3/2006 | Ding et al. |
| 7,505,710 | B2 | 3/2009 | Harlev et al. |
| 7,620,447 | B2 | 11/2009 | Harel et al. |
| 7,912,544 | B1 | 3/2011 | Min et al. |
| 8,224,432 | B2 | 7/2012 | Macadam et al. |
| 2004/0220635 | A1 | 11/2004 | Burnes |
| 2006/0293603 | A1 | 12/2006 | Strandberg |
| 2006/0293714 | A1 | 12/2006 | Salo et al. |
| 2007/0088401 | A1 | 4/2007 | Spinelli et al. |
| 2007/0208260 | A1* | 9/2007 | Afonso ............... A61B 5/287 600/300 |
| 2008/0243202 | A1 | 10/2008 | Patangay et al. |
| 2009/0053102 | A2* | 2/2009 | Rudy ................... A61B 5/318 422/186.3 |
| 2009/0318995 | A1 | 12/2009 | Keel et al. |
| 2010/0069987 | A1 | 3/2010 | Min et al. |
| 2010/0222836 | A1 | 9/2010 | Jarverud |
| 2011/0190649 | A1* | 8/2011 | Rudy ................... A61B 5/316 600/509 |
| 2011/0213260 | A1 | 9/2011 | Keel |

FOREIGN PATENT DOCUMENTS

| | | |
|---|---|---|
| WO | 2006039693 A1 | 4/2006 |
| WO | 2006105474 | 10/2006 |
| WO | 2007087025 A1 | 8/2007 |
| WO | 2008118349 | 10/2008 |
| WO | 2008121185 A1 | 10/2008 |
| WO | 2009114447 A1 | 9/2009 |
| WO | 2009137502 | 11/2009 |

OTHER PUBLICATIONS

A. Auricchio, "Characterization of Left Ventricular Activation in Patients with Heart Failure and Left Bundle-Branch Block", Circulation, vol. 109, No. 9, Mar. 1, 2004, pp. 1133-1139.

P.D. Lambiase, et al., "Non-contact Left Ventricular Endocardial Mapping in Cardiac Resynchronisation Therapy", Heart, vol. 90, No. 1, Jan. 1, 2004, pp. 44-51.

David R. Sutherland, et al., "Experimental Measures of Ventricular Activation and Synchrony", Pacing and Clinical Electrophysiology, vol. 31, No. 12, Dec. 1, 2008, pp. 1560-1570.

Tanaka H., et al., "Comparative Mechanical Activation Mapping of RV Pacing to LBBB by 2D and 3D Speckle Tracking and Association with Response to Resynchronization Therapy", JACC: Cardiovascular Imaging, Elsevier, Amsertdam, NL, vol. 3, No. 5, May 1, 2010, pp. 461-471.

Rudy, et al., "Noninvasive Electrocardiographic Imaging of Cardiac Resynchronization Therapy in Patients with Heart Failure", Journal of Electrocardiology, Elsevier Science, XX, vol. 39, No. 4, Oct. 1, 2006, pp. S28-S30.

Kyungmoo Ryu, et al., "Simultaneous electrical and Mechanical Mapping Using 3D Cardiac Mapping System: Novel Approach for Optimal Cardiac Resynchronization Therapy", Journal of Cardiovascular Electrophysiology, vol. 21, No. 2, Feb. 1, 2010, pp. 219-222.

F. Regoli, et al., "The Role of Invasive Mapping in the Electrophysiology Laboratory", Europace, vol. 11, No. Supplement 5, Oct. 27, 2009, pp. v40-v45.

J. Kautzner, et al., "Selecting CRT Candidates: The Value of Intracardiac Mapping", Europace, vol. 10, No. Supplement 3, Nov. 1, 2008, pp. iii106-iii109.

Cardioinsight Technologies, Inc., "Supplementary European Search Report", Application No. EP 11838817, dated Apr. 28, 2014, 11 pgs.

* cited by examiner

SYSTEMS AND METHODS FOR ASSESSING HEART FUNCTION

RELATED APPLICATION

This application is a continuation of U.S. application Ser. No. 15/805,903, filed Nov. 7, 2017, and entitled "SYSTEMS AND METHODS FOR ASSESSING HEART FUNCTION," which is a continuation of U.S. application Ser. No. 14/798,124, filed Jul. 13, 2015, and entitled "SYSTEMS AND METHODS FOR ASSESSING HEART FUNCTION," which is a continuation of U.S. application Ser. No. 13/882,912, filed May 1, 2013, and entitled "SYSTEM AND METHODS FOR ASSESSING HEART FUNCTION," which is a 371 of PCT/US2011/059174, filed Nov. 3, 2011, which claims the benefit of U.S. provisional patent application No. 61/409,714 filed Nov. 3, 2010, and entitled "SYSTEM AND METHODS FOR ASSESSING HEART FUNCTION," each of which is incorporated herein by reference in its entirety.

TECHNICAL FIELD

This disclosure relates to systems and methods for assessing heart function.

BACKGROUND

The normal electrical conduction of the heart allows electrical propagation to stimulate the myocardium. Time ordered stimulation of the myocardium allows efficient contraction of all four chambers of the heart, thereby allowing selective blood flow through both the lungs and systemic circulation. The ordered stimulation can become de-synchronized and thereby adversely affect the mechanical function of the heart.

Cardiac resynchronization therapy (CRT) is a method of improving the mechanical function of the heart using electrical therapy (e.g., pacing both the right and left ventricles). Various techniques are utilized to determine a pacing site as well as to determine pacing parameters. Current mechanical and electrical measures tend to be qualitative and are highly operator dependent due to the complex nature of ventricular activation and the lack of quantitative comparisons between electrical activation and mechanical function.

SUMMARY

This disclosure relates to systems and methods for assessing heart function, such as based on sensed electrical activity.

As an example, a method for assessing a function of the heart can be provided. The method can include determining a time-based electrical characteristic for a plurality of points distributed across a spatial region of the heart. The plurality of points can be grouped into at least two subsets of points based on at least one of a spatial location for the plurality of points or the time-based electrical characteristics for the plurality of points. An indication of synchrony for the heart can be quantified based on relative analysis of the determined time-based electrical characteristic for the at least two subsets of points. The method can be embodied as instructions stored in a machine readable medium that can be also be executed by a processor.

As another example, a system can include memory to store data and machine-executable instructions. The stored data can electrical data representing electrical signals for a plurality of points spatially distributed across a cardiac envelope over a period of time. A processor can access the memory and execute the instructions. When such instructions are executed, they cause the processor to quantify an indication of synchrony for a patient's heart based on analysis of a first set of the electrical data associated with a first subset of the plurality of points relative to a second set of set of the electrical data associated with a second subset of the plurality of points.

DETAILED DESCRIPTION

This disclosure relates to systems and methods for assessing the function of the heart. The systems and methods can be employed to provide a quantitative assessment of heart function (e.g., synchrony) that is computed based on electrical information for one or more regions of the heart.

As an example, the systems and methods can be utilized to evaluate a function of the heart based on electrical activity distributed across one or more spatial regions of the heart. The regions can include segmented regions (also referred to herein as segments) within one or more chambers of the heart. The evaluation further can include comparative or correlative statistics for the electrical activity among multiple heart chambers, such as may include the left and right chambers (e.g., ventricles) of the heart.

As another example, the quantitative analysis can be computed to output one or more indices that quantify activation time heterogeneity and/or repolarization time heterogeneity. For instance, one or more indices can be computed to include one or more of a Global Interventricular Synchrony (GIS) Index, a Segmental Synchrony Index (SIS), an Intraventricular Conduction Index (ICI) or a late activation (LAI) index. Each index can be calculated based solely on measured electrical activity (e.g., without the need for mechanical data for the heart). For instance, the electrical activity can be measured via non-invasive methods. Systems and methods can generate graphical outputs based on these or other indications of synchrony to facilitate the assessment of cardiac function.

The quantitative assessment of synchrony can also be utilized to facilitate delivery of a therapy. For example, an indication of cardiac synchrony can be computed intraoperatively and used to guide administration of therapy to the patient (e.g., providing closed loop feedback during delivery of therapy). The guidance can include spatial guidance to locate one or more sites to which the therapy may be applied. Additionally or alternatively, the guidance can provide information to set and/or provide automated control for therapy parameters (e.g., a quantity and duration of a given therapy as well as a delay time between delivery of consecutive therapies).

As one example, the index can be computed used to guide CRT therapy, such as taking into account both the delivery method (the accessible locations where a pacing lead can be anchored) and providing information about the health of the substrate. For determining the treatment parameters (e.g., location as well as stimulation parameters), each treatment parameter can be varied for a given patient and the index computed for a plurality of different treatment parameters. This process can be repeated and the results evaluated to ascertain treatment parameters to achieve desired therapeutic effect.

Figure 1:
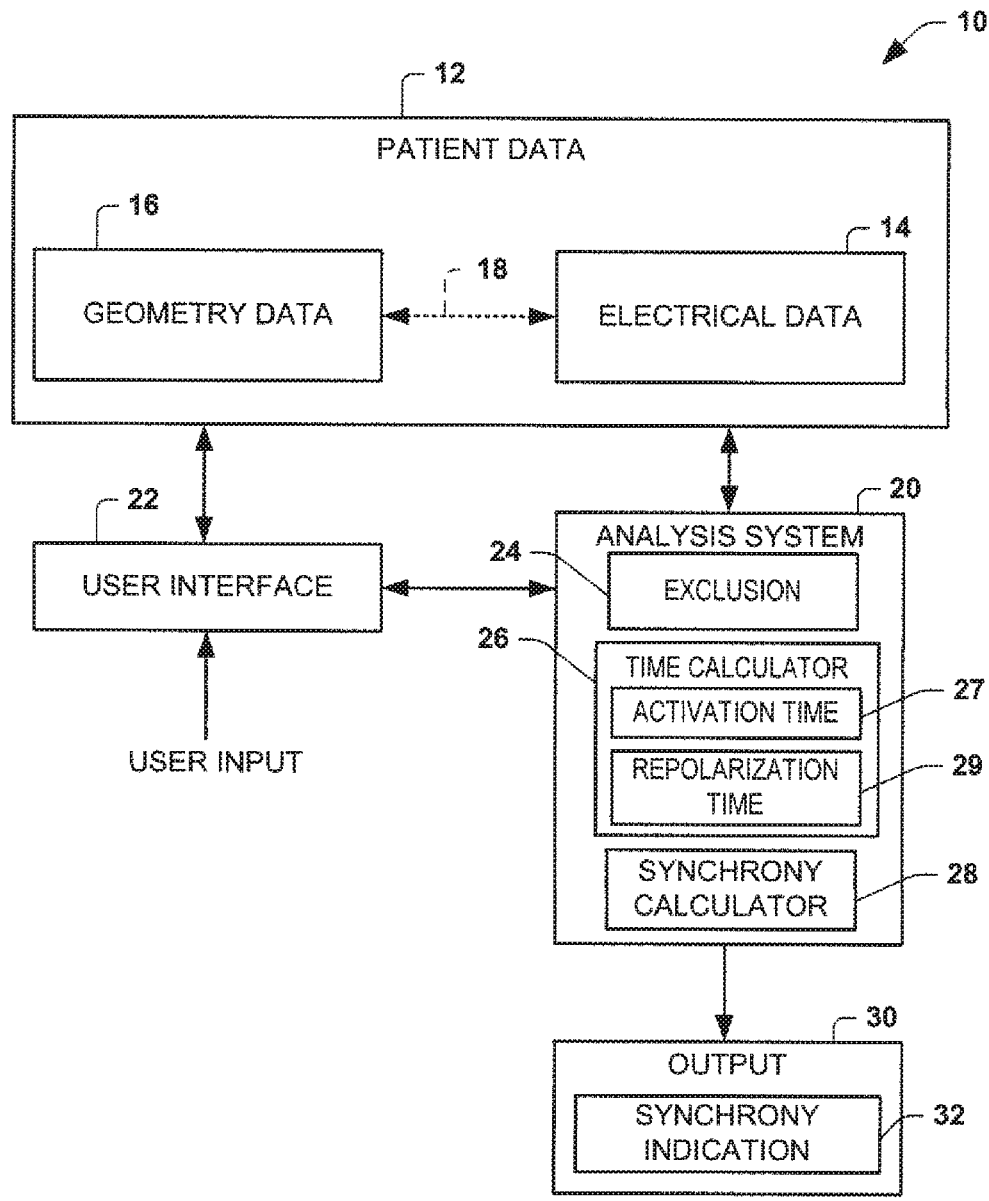
FIG. 1 depicts an example of a system that can be implemented to ascertain an indication of heart function.

FIG. 1 depicts an example of a system 10 for assessing cardiac function of a patient. The system 10 can be implemented in a standalone computer, a workstation, an application specific machine, or in a network environment in which one or more of the modules or data can reside locally or remotely relative to where a user interacts with the system 10.

The system 10 employs patient data 12 for one or more patient, such as can be stored in an associated memory device (e.g., locally or remotely). The patient data 12 can include electrical data 14 that represents electrical information for a plurality of points, each of which is indexed or otherwise programmatically associated with (e.g., linked to) an anatomical geometry of the patient. The patient data 12 can also include geometry data 16, such as can be embodied as a geometry model for a three-dimensional region of anatomy. The model can be a generic model, which can be tailored for a given patient based on measurements and/or imaging data for the patient. Alternatively, the geometry data can be a patient-specific model that is generated based on imaging data for the patient. In one example, the geometry data 16 can correspond to a surface of model of a given patient's entire organ, such as the heart, which can be graphically rendered as a two- or three-dimensional representation.

The patient electrical data 14 can be raw data, such as has been collected from an electrophysiology mapping catheter or other means that can be utilized to acquire electrophysiology data for a selected region of a patient (e.g., of an organ, such as the heart). Additionally or alternatively, the electrical data 14 can correspond to processed data, such as can be computed from raw data to provide electrophysiology information for the selected region of the patient (e.g., a cardiac envelope for the heart).

By way of example, non-invasive electrophysiological mapping (e.g., electrocardiographic (EC) mapping for the heart) can be performed on a body surface of the patient to generate the electrical data 14. This technique can generate electrophysiological data by combining body surface electrical measurements with patient geometry information through an inverse method programmed to reconstruct the electrical activity for a predetermined surface region of the patient's heart. Thus, the results of the inverse method can provide the corresponding electrical data 14 that is registered with the patient geometry data 16. Thus, the electrical data 14 can represent reconstructed electrical signals (e.g., time-based electrical potentials) for each of the plurality of points on a cardiac envelope concurrently as a function of time, such as an epicardial surface, endocardial surface or other envelope. Examples of inverse algorithms that can be utilized in the system 10 are disclosed in U.S. Pat. Nos. 7,983,743 and 6,772,004, which are incorporated herein by reference.

In another embodiment, a contact or non-contact electrophysiology catheter can be placed in a patient's heart and collect electrophysiology data at a plurality of spatial locations over time, such as during a number of one or more cardiac intervals. Such data can be spatially and temporarily aggregated in conjunction with image data for the patient's heart to provide the electrical data 14 for corresponding regions of the patient's heart. Alternatively, other devices (e.g., catheters or patches) can be placed on or near a patient's heart, endocardially and/or epicardially, such as during open chest and minimally invasive procedures, to record electrical activity data, which can be mapped to a representation of the patient's heart to provide similar corresponding electrical data 14.

Those skilled in the art will understand and appreciate that the system 10 is equally applicable to patient electrical data 14 that can be gathered and/or derived by any of these or other approaches, which may be invasive or non-invasive. Additionally, it will be understood and appreciated that the electrical data 14 can be provided in any form and converted into an appropriate form for processing in the system 10.

As mentioned above, the system 10 also employs geometry data 16, such as can represent a predetermined surface region of an anatomical structure, which can be a generic structure or be specific for a given patient. For example, the geometry data 16 can correspond to a patient-specific representation of a surface of an organ or other structure to which the patient electroanatomical data has been registered. For instance, the geometry data 16 may include a graphical representation of a region of the patient's organ, such as can be generated by appropriate image processing of image data acquired for the patient. Such image processing can include extraction and segmentation of an organ from a digital image set. The segmented image data thus can be converted into a two-dimensional or three-dimensional graphical representation of a surface region of the patient's organ. Alternatively, the patient geometry data 16 can correspond to a mathematical model, such as can be constructed based on image data for the patient's organ. Appropriate anatomical or other landmarks can be associated with the organ represented by the anatomical data for the organ to facilitate subsequent processing and visualization in the system 10.

As mentioned above, the electrical data 14 can be registered into a common coordinate system with the patient geometry data 16. For instance, the electrical data 14 can be stored in a data structure of rows (corresponding to different anatomical points) and columns (corresponding to samples) in which the rows of data have the same index as (or are registered to) respective points residing on patient geometry data 16. This registration or indexed relationship between the electrical data 14 and the geometry data 16 is indicated by a dashed line at 18. In one embodiment, the samples in each of the columns can represent simultaneous information across the entire surface region (e.g., the heart) of the patient.

The geometry data 16 can be generated from image data that is acquired using nearly any imaging modality. Examples of imaging modalities include ultrasound, computed tomography (CT), 3D Rotational angiography (3DRA), magnetic resonance imaging (MRI), x-ray, positron emission tomography (PET), and the like. Such imaging can be performed separately (e.g., before or after the measurements) utilized to generate the electrical data 14. Alternatively, imaging may be performed concurrently with recording the electrical activity that is utilized to generate the patient electrical data 14.

It will be understood and appreciated by those skilled in the art that the system 10 is equally applicable to employ anatomical data that may be acquired by any one of these or other imaging modalities. The type of imaging modality can vary according to the purpose or purposes of the data 16. For example, CT provides an effective modality for use in performing the inverse method in conjunction with body surface electrodes used in performing electrical measurements for generating the electrical data 14 as EC mapping data. MR imaging is useful for identifying areas of scar in the heart, such as for identifying areas (e.g., scar areas) to be excluded from subsequent processing and evaluation, as disclosed herein. Thus, one or more image sets can be acquired by one or more imaging modalities, each of which can be co-registered with and collectively stored as the patient geometry data 16.

Alternatively or additionally, the geometry data 16 can correspond to a generic or custom representation of an organ, which may not be the patient's own organ. In such a case, the electrical data 14 can be mapped (via registration 18) to the representation of the organ according to identified anatomical landmarks. A manual, semi-automatic or automatic registration process can be employed in order to register the anatomical model with the signal acquisition system, if any.

It further will be understood and appreciated that depending upon the format and type of input data appropriate formatting and conversion to a corresponding type of representation can be implemented by the system 10. For instance, the patient data 12 can include electrical data that is provided to the system 10 in a known format or be converted to a standard format for processing by the system. Thus, the patient data 12 can include an aggregate set of electrical data for the patient.

An analysis system 20 is programmed to compute an assessment of heart function. The analysis system 20 can be implemented as computer-executable instructions implemented on a processor running remotely or locally on a computer where the patient data 12 is stored. A user interface 22 can be utilized to activate or otherwise interact with the analysis system 20 such as for calculating an indication of synchrony, such as described herein. As used herein, the indication of synchrony can be employed to provide a quantitative measure of synchrony for the heart or a measure of dyssynchrony for the heart or a combination of synchrony and dyssynchrony. For purposes of consistency herein, however, such measures are referred to herein as relating to synchrony.

The user interface 22 can provide a graphical and/or other interface that allows a user to provide a user input for initiating the process. The user interface 22 can also be utilized to set and establish data paths and variables employed by the analysis system 20. The user interface 22 can also be utilized to configure the computations performed by the analysis system 20 and/or one or more output devices 30 that can be provided. For instance, the user interface 22 can configure the types of methods and parameters utilized in forming the analysis based on the patient data 12.

The analysis system 20 can also include an exclusion component 24 that identifies areas of patient geometry that are to be excluded. The identified areas can be excluded from analysis (e.g., by making all electrical activity zero for such excluded points) or the identified areas can be removed from the results provided by the analysis system 20. For example, the exclusion component 24 can be employed to identify one or more areas that do not contribute to mechanical function as well as areas that will not respond to stimulation from electrodes. The exclusion component 24 can be programmed as code that is executed to automatically identify areas to be excluded. Alternatively or additionally, the exclusion component 24 can set the one or more areas to be excluded in response to user inputs provided via the user interface 22. The identification of areas to be excluded can be performed based on geometry data 16, patient electrical data 14 as well as based on a combination thereof.

For example, the geometry data 16 can include MRI data for the patient's heart, which can be utilized to identify scar areas. The scar areas can be co-registered with the electrical data 14, and thereby be utilized to exclude such regions from subsequent analysis, such that points in such excluded regions are not utilized by the analysis system 20 in quantifying synchrony. Those skilled in the art will understand and appreciate other types of imaging technology or other means that can be utilized to identify such scar areas.

Additionally or alternatively, the exclusion component 24 can identify electrical properties of areas corresponding to scarring or other regions that may be non responsive to electrical stimulation. For example, the exclusion component 24 may access a subset of methods for computing or otherwise identifying areas of low-voltage electrograms, areas of fractionated electrogram morphology as well as areas of low or erratic conduction rates (dV/dT). The excluded areas can be populated to the electrical data 14 or otherwise utilized in the process for selectively excluding those areas that have been identified for exclusion from analysis.

The analysis system 20 also includes a time calculator 26 that is programmed to compute a temporal characteristic for each of a plurality of points on the cardiac envelope for which the electrical activity has been determined. For instance, the temporal characteristic can be computed for a selected beat (e.g., a sinus beat) or an interval that includes more than one beat. The beat or interval can be selected by the user interface 22 by manual user input. Alternatively or additionally the analysis system 20 can automatically identify and select a beat for which temporal characteristic will be calculated by the time calculator 26. The temporal characteristic thus can be computed for each of the plurality (e.g., thousands) of points on the surface of the heart for the same heart beat or other associated time interval. Additionally, the selected interval can be applied to filter the electrical data 14 such that electroanatomic data is provided for the selected beat.

As demonstrated in the example of FIG. 1, the time calculator 26 can include an activation time calculation component 27 programmed to compute an activation time for the plurality of points on the cardiac envelope. Additionally or alternatively, the time calculator 26 can include a repolarization time calculation component 29 programmed to compute a repolarization time for the plurality of points on the cardiac envelope.

The analysis system 20 also includes a synchrony calculator 28 that is programmed to quantify an indication of synchrony based on the one or more temporal characteristics computed by the time calculator 26 for each of the non-excluded areas of the heart. That is, the synchrony calculator 28 may not compute the indication of synchrony for points on the cardiac envelope determined to reside in excluded areas. Alternatively, depending upon application requirements, indexes can be computed for all points on the cardiac envelope and those indexes computed for excluded areas can be excluded from results and evaluation. In some cases, no areas will be excluded. Those areas of exclusion identified via the exclusion component 24 further can be visualized on an output device 30 such as in a two-dimensional or three-dimensional representation of the patient's heart.

By way of further example, the synchrony calculator 28 can calculate one or more index such as including a global synchrony index (GSI), an intraventricular conduction index (ICI) or a segmental synchrony index (SSI), a late activation index, such as according to the methods disclosed herein. The synchrony calculator 28 computes an indication of synchrony 32 that can be provided to the output device 30 for providing a visualized assessment of a patient's heart function. As described herein, the index 32 can provide an assessment of heart electrical function, heart mechanical function, hemodynamic performance or any combination thereof.

As one example, the synchrony calculator 28 computes a quantitative measure of electrical synchrony as a global synchrony index (GSI). As one example, the global synchrony index provides a measure of synchrony based upon statistical analysis of activation times for the left ventricle relative to the right ventricle of the patient's heart. For example, the synchrony calculator 28 can compute the GSI by computing the mean and standard deviation of activation times for each ventricle. The GSI index thus corresponds to the difference between the mean activation times for the left and right ventricle as well as the standard deviation between the right and left ventricles. As an example, the GSI for the mean and standard deviation calculations can be computed as follows:

$GSI_M$=mean(RV activation times)−mean(LV activation times)

$GSI_{SD}$=RV standard deviation−LV standard deviation where the designation RV and LV can mean whole chamber or a selected part of the chamber (e.g., such as the free wall).

This GSI can be utilized for determining location and stimulation parameters for CRT. For determining an optimal lead location, the analysis system 20 can repeat GSI computations for paced beats at different stimulation parameters and different locations. The locations can further take into account that the delivery of method and the health of the substrate at which the patient is being applied. A desired site can be the site determined to have lowest $GSI_M$ index, the lowest $GSI_{SD}$ index or having the lowest combination of indices. Treatment parameters for CRT can be determined in a similar manner in which parameters at one or more locations can be adjusted and corresponding GSI data computed. Corresponding parameters can be selected based upon their evaluations comparing respective GSI indices computed for each set of parameters.

Figure 2:
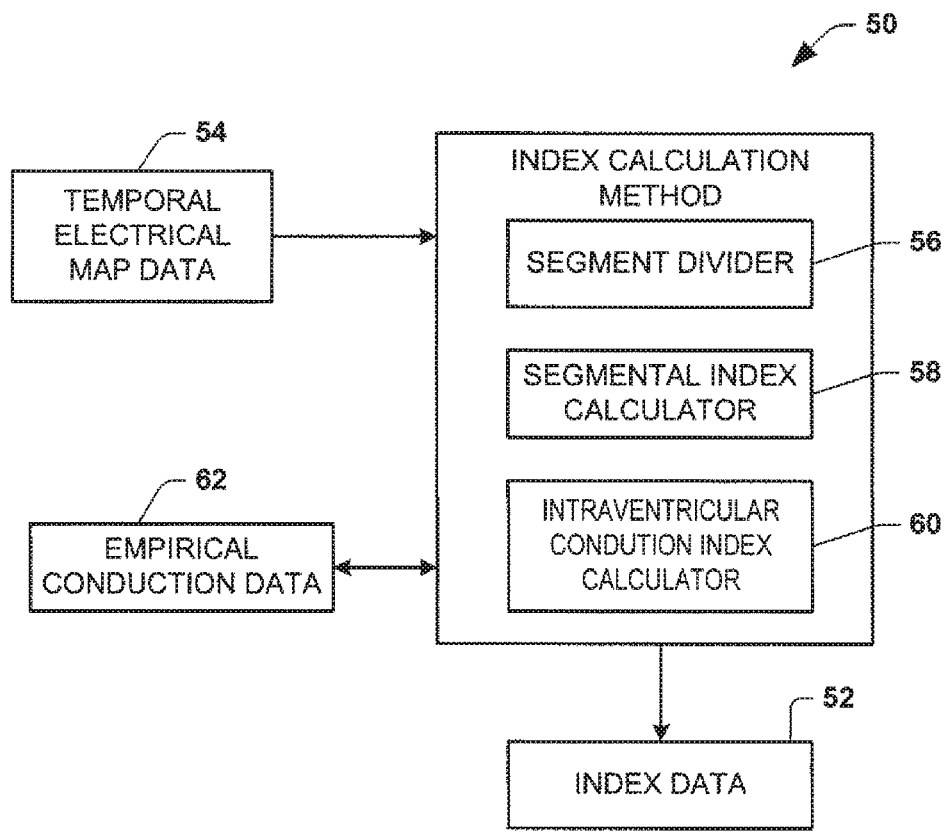
FIG. 2 depicts an example of a calculator that that can be implemented to compute a first index indicative of heart function.

FIG. 2 depicts an example of another index calculation method 50 that can be utilized to compute an index that is referred to herein as an intraventricular conduction index (ICI). The index calculation method 50 provides the index as index data 52. The index calculation method 50 computes the index data based on map data 54, such as activation and/or repolarization data disclosed herein with respect to FIG. 1. The ICI index provides a quantitative measure of electrical synchrony relative to established normal synchrony for each of a plurality of different segments determined for the heart.

The index calculation method 50 can employ empirical conduction data 62. The conduction data 62 can include activation and/or repolarization times derived based on clinical or other forms of investigation for a patient population known to have normal conduction patterns. As an example, the empirical conduction data 62 can be represented as a normal segmental index associated with the plurality of patients that form a patient population. The patient population further may be arranged or otherwise sortable according to patient health parameters, age parameters, height or other criteria that can be utilized to generate customized relevant patient populations corresponding to a normal class of people consistent with the particular attributes of a given patient for which the index calculation method 50 is being performed. The selection of the conduction data can be automated based on attributes entered for the given patient or the conduction can be manually selected for a given patient.

In the example of FIG. 2, the index calculation method 50 includes a segment divider 56 that is programmed to divide right and left portions (e.g., ventricles) of the heart into a respective plurality of N segments, where N is a positive integer denoting a number of segments (e.g., anatomical regions) into which each ventricle is divided. Examples of the segments for each ventricle can include, for example the apex region, outflow tract, or the like.

Figure 3:
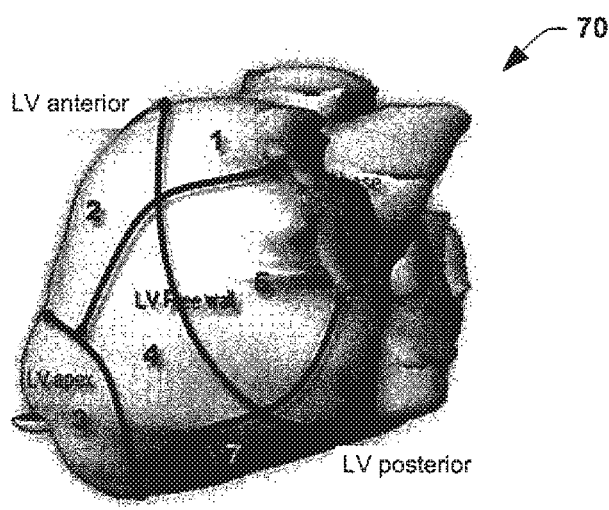
FIG. 3 depicts part of a heart demonstrating an example of segmenting the heart into regions.

FIG. 3 depicts an example of a graphical representation of the heart 70 demonstrating an approach where the left ventricle is divided anatomically into a plurality (e.g., seven) of segments. Those skilled in the art will understand and appreciate various types of segments into which each ventricle can be divided, which can correspond to solely anatomical regions, such as shown in the example of FIG. 3. Alternatively, different chambers of the heart, including the ventricles, can be divided into segments according to an expected contribution to hemodynamic performance, or mechanical function. As yet another alternative, the heart can be geometrically divided into segments that can be of equal size or the sizes of such segments can be different. The different segments of the heart can correspond to contiguous anatomical regions or a given segment may include a non-contiguous set of points distributed across the heart.

In one embodiment each of the segments of the heart can be selected according to an expected contribution to hemodynamic function for each of the respective anatomical regions of the corresponding ventricles. In this way certain segments of each ventricle that contribute commensurately to hemodynamic and mechanical function of the heart can be grouped together into a given segment. Corresponding EC mapping data (e.g., time-indexed reconstructed electrical activity data) for points residing within each region can thus be grouped together (e.g., tags or indices) for each respective region for use in performing the index calculation method 50.

The index calculation method 50 also includes a segmental index calculator 58 that is programmed to compute one or more segmental indices for each of the N segments into which the right and left ventricles (or other anatomical portions have been divided (e.g., by the segment divider 56). For instance, the segmental index calculator 58 can compute one or more segmental indices based on evaluation of activation map data that has computed and aggregated into the respective N segments for each ventricle for a given beat. The indices can be calculated from statistical evaluation of time-based electrical activity data (e.g., corresponding to activation time and/or repolarization times) for points within each segment. For the example of activation time data, the index calculator 58 can compute the segmental index to include a mean activation time for each segment as well as a standard deviation for each respective segment. The corresponding segmental indices can be stored in memory.

As mentioned above, the empirical conduction data 62 for each of the N segments can also be stored in memory for use in computing the ICI. The normal conduction delays can be stored in memory for each of the N segments based upon corresponding statistical analysis for respective segments for a normal population of patients. For instance, the empirical conduction data 62 can provide a statistical representation for a normal patient population, such as the mean activation time and standard deviation of activation time for each of the N segments. Each of the N values of the conduction data can be linked or otherwise programmatically associated with each of the values computed for the N regions by the segmental index calculator 58.

The intraventricular conduction index calculator 50 is programmed to compute the ICI index to represent contributions from each of the N segments of the left and right ventricles as a function of the normal conduction delays and the corresponding segmental indexes computed by the segmental index calculator for each of the N segments. As one example, the ICI indices may be computed as follows:

$$ICI_m = ICI_{mLV} - ICI_{mRV} = [\text{sum ABS}(SI(n)_m - N(n)_m) \text{ for all segments } n \text{ in LV}] - [\text{sum ABS}(SI(n)_m - N(n)_m) \text{ for all segments } n \text{ in RV}]$$

$$ICI_{sdLV} = \text{sum ABS}(SI(n)_{sd} - N(n)_{sd}) \text{ for all segments } n \text{ in LV}$$

$$ICI_{sdRV} = \text{sum ABS}(SI(n)_{sd} - N(n)_{sd}) \text{ for all segments } n \text{ in RV}$$

$$ICI_{sd} = ICI_{sdLV} - ICI_{sdRV}$$

The intraventricular conduction index calculator 50 in turn generates a corresponding ICI index, including one or any combination of the $ICI_M$, $ICI_{sdLV}$, $ICI_{sdRV}$, and $ICI_{SD}$. The corresponding index or indices can be stored as index data 52 for the interval for which the activation time corresponds. Corresponding index data 52 can be computed for a plurality of different beats and patient conditions.

As one example, the index data 52 can be computed for a variety of different pacing lead/electrode locations to identify which location can help improve synchrony. The calculations and locations can take into account both delivery method and the health of the substrate for a given location. A desired therapy site thus can be determined based upon an evaluation or comparison of the respective ICI indices computed for each of a plurality of locations. For example, the lowest $ICI_M$ index, the lowest $ICI_{SD}$ index or a combination of respective indices can be utilized to determine the desired pacing site or lead location. Similarly, the ICI indices can be computed for determining optimal treatment parameters. For instance, ICI indices can be computed for a plurality of different treatment parameters (e.g., for programming a CRT device) and the parameters that minimize the ICI index can be utilized to determine an optimal or desired set of treatment parameters.

As another example, a patient's candidacy for cardiac therapy can be evaluated based on the index data 52. For instance, a level of a patient's dyssynchrony can be determined based on a dispersion of activation, such as represented in one or more of the $ICI_{sdLV}$, $ICI_{sdRV}$, and $ICI_{SD}$ indices. Thus, the indices can be compared relative to corresponding thresholds to qualify a patient as a candidate for cardiac therapy, such as including CRT.

Figure 4:
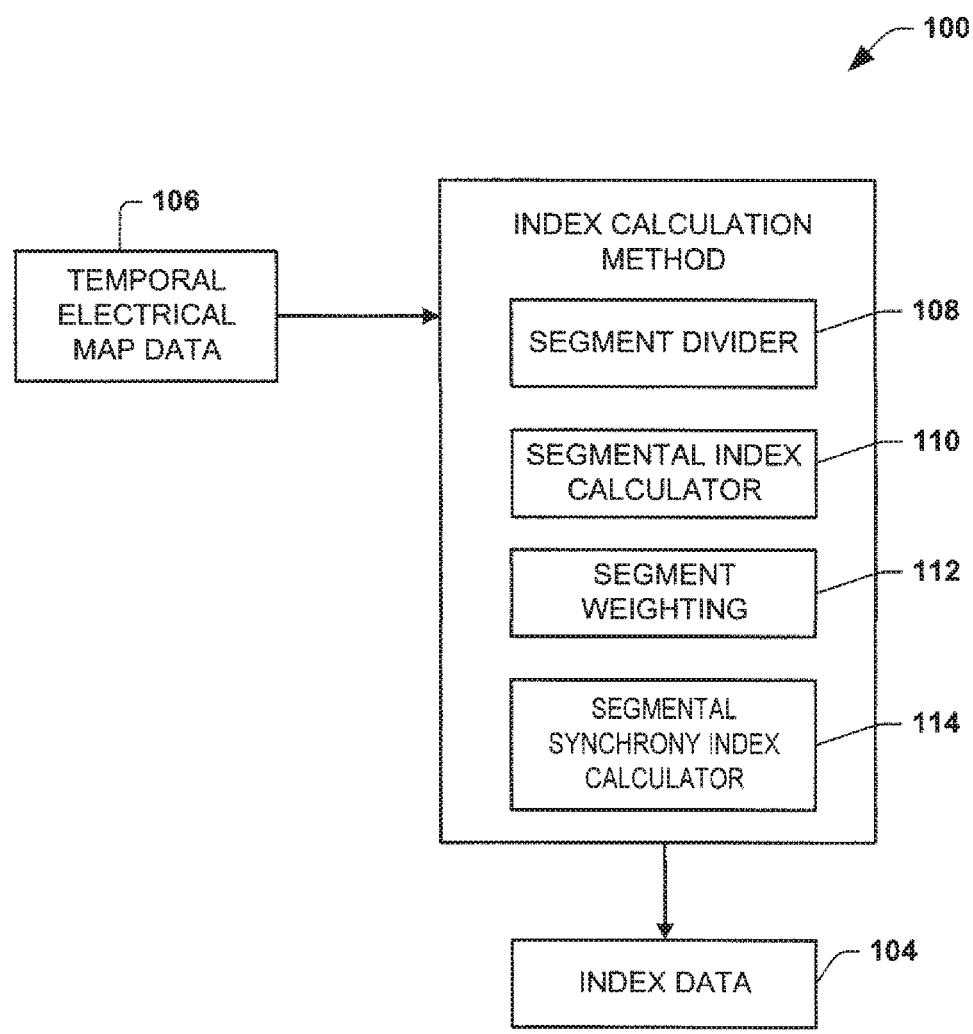
FIG. 4 depicts an example of a calculator that that can be implemented to compute a second index indicative of heart function.

FIG. 4 depicts an example of another index calculation method 100 that can be utilized to compute index data 104, which is referred to in this example as including a segmental synchrony index (SSI). The SSI index provides an assessment of mechanical synchrony based on electrical measurements. The index calculation method 100 can computes the SSI based on electrocardiographic map data 106, such as can be determined from measured electrical activity as shown and described herein. The map data 106 can represent the activation time and/or repolarization time (or other time-based electrical characteristic) for each of a plurality of points on a cardiac envelope over one or more beats.

In the example of FIG. 4, the index calculation method 100 includes a segment divider 108 that is programmed to divide the anatomical regions of the heart into N segments, such as described with respect to FIGS. 2 and 3. The time based electrical characteristics represented by the map data can be classified and processed according to which segment it belongs. There can be any number of N regions, which may be established according to known anatomical regions (e.g., the apex, outflow tract and the like). The regions can represent contiguous or non-contiguous anatomical areas of the heart.

The index calculation method 100 also includes a segmental index calculation 110 that is programmed to calculate a statistical assessment for each of the N segments based on the map data for points on the heart residing in each of the respective segments. For instance, the segmental index calculator 110 can calculate a mean and standard deviation of the time-based electrical characteristics (e.g., activation time and/or repolarization time) for each of the plurality of points (in the map data 106) within each of the N region for each ventricle. For the example of activation time as the time-based electrical characteristic, the SI for each segment N can be determined, as follows:

$SI(N)_M$=mean activation time in segment $N$

Similarly, a segmental dispersion of intraventricular activation can be determined for each of the LV and RV, as follows:

$SI(N)_{SD\_LV}$=standard deviation for each segments $N$ in LV $SI(N)_{SD\_RV}$=standard deviation for each segment $N$ in RV The above calculations for the SSI indices can be computed for each of the respective N segments in the left and right ventricles. The segmental dispersion further can be employed to identify a segment having an increased dispersion relative to other segments.

The SSI can provide an assessment of mechanical synchrony based on electrical measurements by weighting each of a plurality of N segments in each ventricle according to its contribution to mechanical heart function and/or hemodynamic performance. Thus, the index calculation method 100 employs segment weighting function 112. The weighting function 112 can be represented as SI(n)w, which provides a value estimating the relative contribution that each given segment N makes to mechanical function and/or hemodynamic performance. As an example, the weighting function SI(n)w for each of the N segments can be calculated for each anatomical region from wall motion imaging (e.g., CT, MRI, fluoroscopy, 2-D or 3-D echocardiograms, or the like). The corresponding weight function 112 can thus be determined and stored in memory associated with each of the N segments of the heart.

The index calculation method 100 also includes a segmental synchrony index calculator 114 that is programmed to compute the SSI index for each of the N segments. For example, a corresponding SSI can be computed for the left ventricle of a given segment and for the right ventricle of the corresponding segment and the corresponding difference between the respective segments of each ventricle computed for each of the corresponding segments. The respective results for each segment can be summed together to provide an indication of the SSI for a patient's heart. For instance, the SSI computed for a given one of the N segments can be multiplied by the corresponding weight for such segment, as provided by the segment weighting function 112. This can be performed for each of the N segments. The SSI can be computed as the mean and standard deviation. For example, the SSI can be calculated as follows:

$$SSI_M = SSI_{MLV} - SSI_{MRV} = [\text{sum}(SI(n)_M * SI(n)_W), \text{ for all segments } n \text{ in LV}] - [\text{sum}(SI(n)_M * SI(n)_W), \text{ for all segments } n \text{ in RV}]$$

$$SSI_{SDLV} = \text{sum}(SI(n)_{SD} * SI(n)_W), \text{ for all segments } n \text{ in LV}$$

$$SSI_{SDRV} = \text{sum}(SI(n)_{SD} * SI(n)_W), \text{ for all segments } n \text{ in RV}$$

$$SSI_{SD} = SSI_{SDLV} + SSI_{SDRV} \text{ for all segments } n \text{ in whole heart}$$

The index calculation method in turn provides corresponding index data such as the SSI which may include the SSI mean and SSI standard deviation based on the activation map data for a given heart beat or interval. As described herein, portions of the heart can be excluded from analysis based upon an identification of scar areas or other areas determined to have a negligible contribution to mechanical and/or electrical function.

The index data 104 can be utilized to determine therapy parameters to achieve a desired therapeutic result for a given patient. For instance, the therapy parameters (e.g., location and stimulation parameters) can be determined based upon an evaluation of the respective SSI indices computed for set of different therapy parameters. For example, the highest $SSI_M$, the lowest $SSI_{SD}$ index or a combination of respective indices can be utilized to determine a desired lead location and stimulation parameters.

Figure 5:
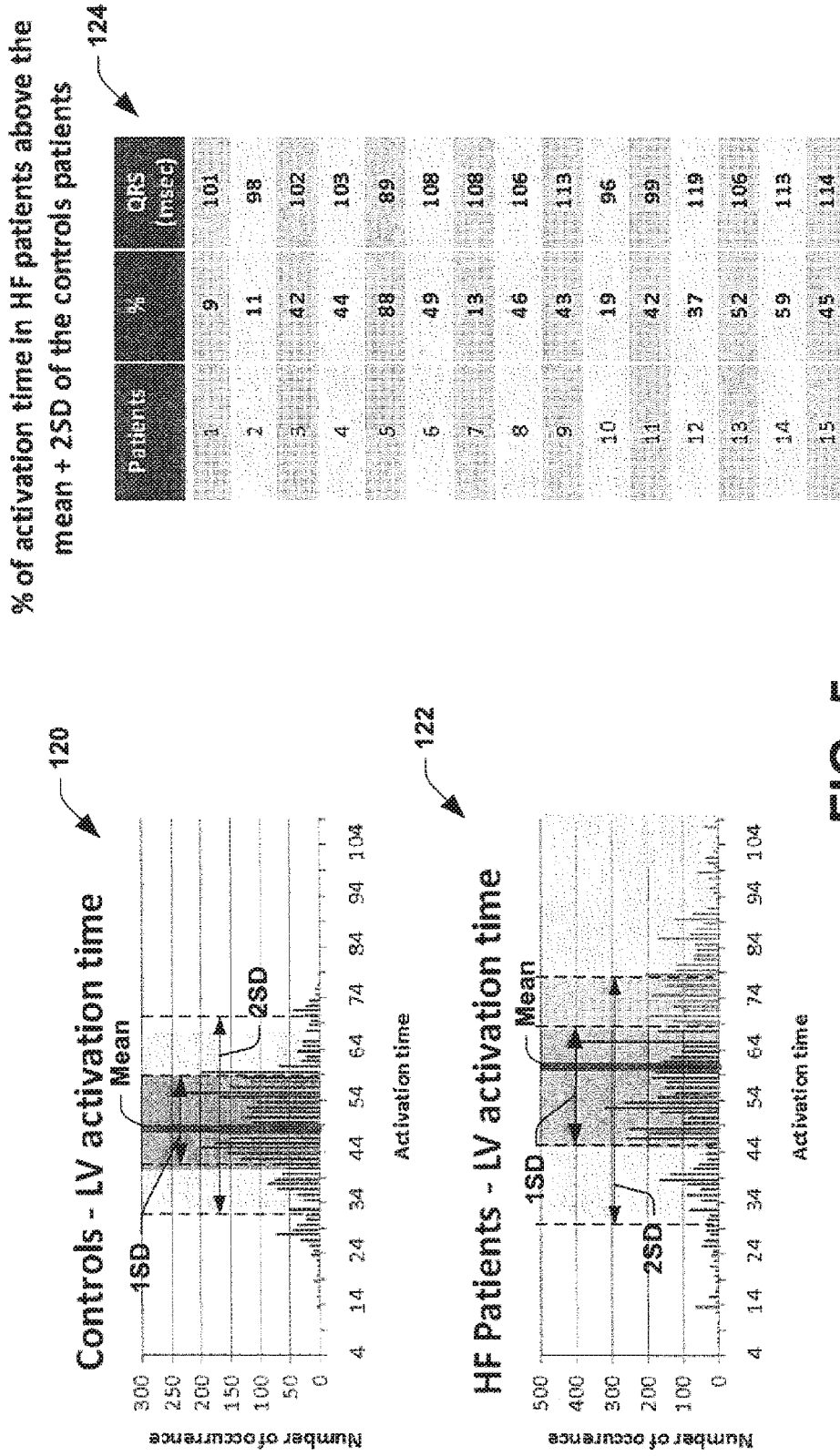
FIG. 5 depicts examples of histogram data that can be utilized in a system or method.
Figure 6B:
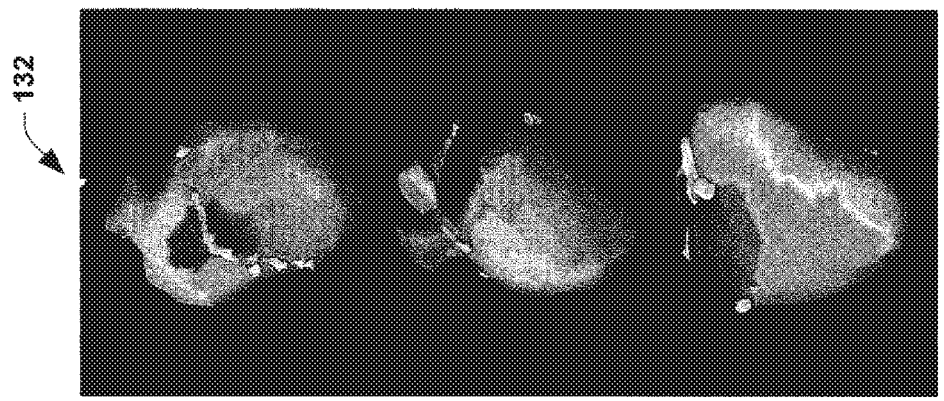
FIGS. 6A and 6B depict examples of maps that can be generated from electrocardiographic mapping for use in ascertaining an indication of heart function.
Figure 6A:
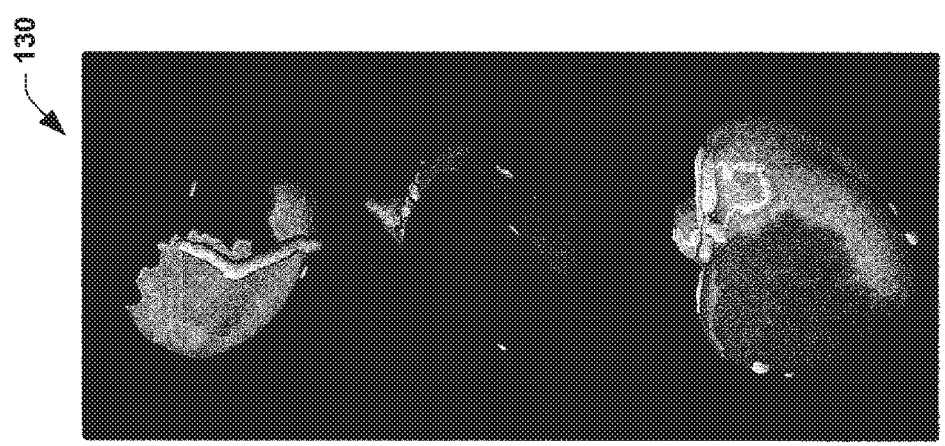
Figure 6A:

FIGS. 5 and 6 will be utilized to illustrate the concept of histogram analysis of activation time. For example, a histogram of activation times can be determined to quantify a percentage of the ventricle is finishing after a set threshold (e.g., 1SD or 2SD) from the mean. The histogram analysis can be applied intraventricularly (within the right or left ventricle) or interventricularly (between ventricles—over the whole heart). Additionally, histogram analysis can be utilized to set one or more thresholds, such as thresholds for any of the indices shown and described herein. As described herein the thresholds can be utilized to select patients as candidates for cardiac therapy.

FIG. 5 depicts an example of information determined from quantitative analysis of heart failure patients. FIG. 5 depicts a histogram 120 of activation time for left ventricles of a control population and a histogram 122 of activation time for a set of patients. Plotted on each histogram are the mean and a first standard deviation (1SD) and a second standard deviation (2SD). By selecting a control population for the histogram 120 from a normal or healthy group (e.g., patients with normal ventricles, LVEF>50% and QRS duration<100 ms), statistical values for the normal population can be determined, such as the MEAN+1SD or MEAN+2SD or another related value. The statistical value can be employed to define one or more thresholds. The histogram data for each of the patients (from histogram 122) can be employed to evaluate their activation time relative to the threshold, such as shown in the table 124 in FIG. 5. For instance, the table 126 shows the percentage of activation time for each patient's left ventricle that exceeds the MEAN+2SD determined from the control histogram 120. Also shown is the QRS duration for each of the patient's. Thus, the histogram analysis can provide a further way to evaluate electrical dyssynchrony for each patient, which may be in addition to QRS duration or other existing criteria.

As described herein, this evaluation can be performed to evaluate the candidacy of each of the patients for cardiac therapy, such as including CRT. There may be a percentage in the control histogram (e.g., a threshold) above which there a patient has little likelihood of responding to therapy. Accordingly, one or more thresholds can also be derived to help identify patient's that would be non-responders to such cardiac therapy as to screen out patient that otherwise might appear good candidates in view of other relevant factors.

FIGS. 6A and 6B depict examples of isochrone maps for different view of the heart, namely an anterior view, the left ventricular free wall and the posterior view of a heart. The isochrone maps on the left side are for a first patient (e.g., having a QRS duration of approximately 89 ms) and the maps on the right side of the figure are for a second patient (e.g., having a QRS duration of 108 ms). A physician thus can compare (e.g. in real-time or otherwise) activation maps as well as other data herein to quantitatively analyze, for example, activation time for each patient as part of a patient screening or other evaluation of heart function.

Figure 7:
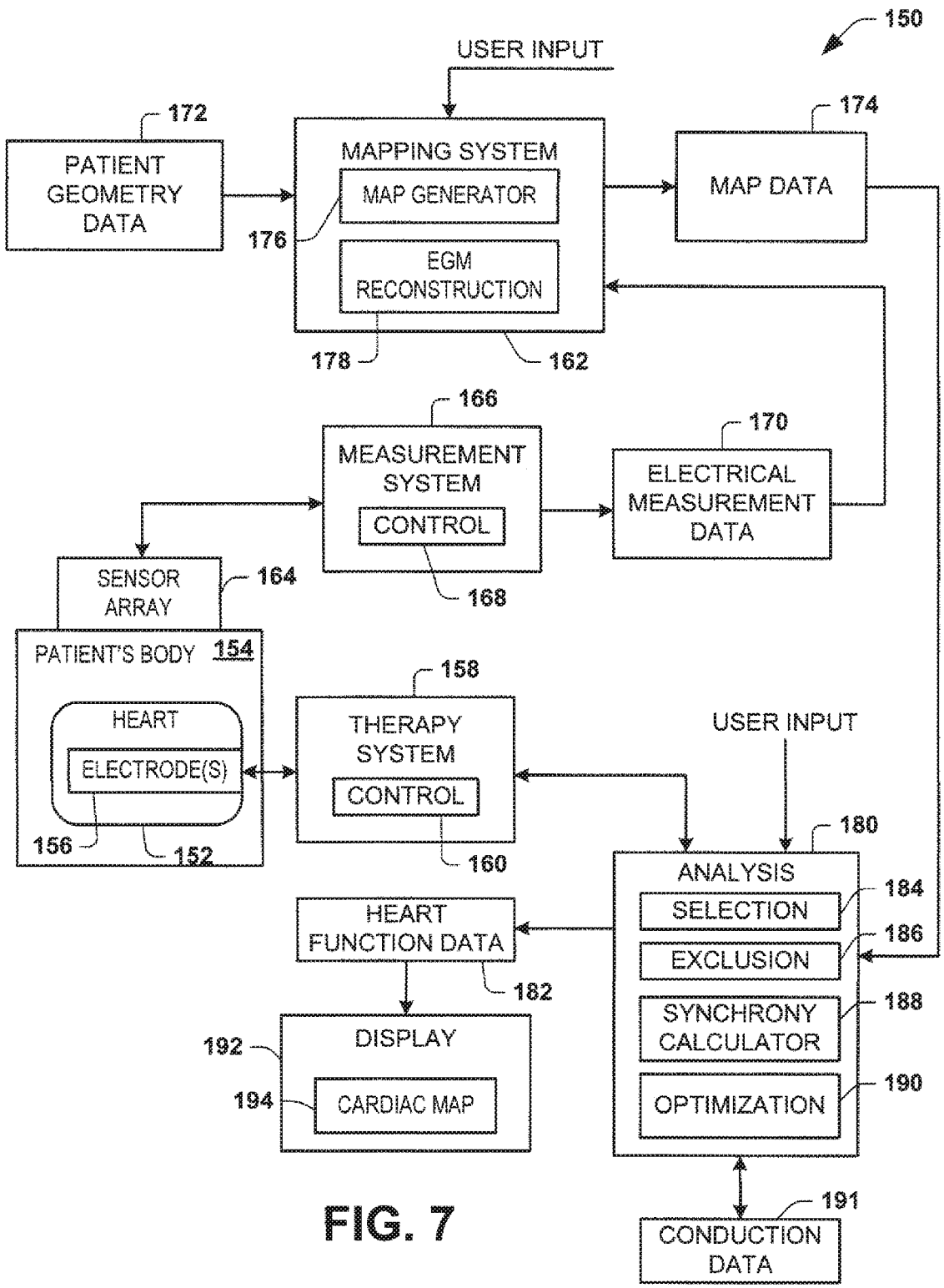
FIG. 7 depicts example of a system that can be implemented to ascertain an indication of heart function to facilitate delivery of a therapy.

FIG. 7 depicts another embodiment of a system 150 that can be utilized for assessing the function of a patient's heart 152, which has been inserted within a patient's body, schematically depicted at 154. The system 150 can perform the assessment of the heart 152 in real time as part of a diagnostic or treatment procedure, such as to help a physician determine parameters for delivering a therapy to the patient (e.g., delivery location and amount and type of therapy). For example, a catheter, such as a pacing catheter, having one or more electrodes 156 affixed thereto can be inserted into the body 154 as to contact the patient's heart 152, endocardially or epicardially. Those skilled in the art will understand and appreciate various type and configurations of pacing catheters and EP catheters that can be utilized to position the electrode(s) 156 in the patient's body 154.

The therapy system 158 controls therapy delivered by the electrode(s) 156. For instance, the therapy system 158 includes control circuitry 160 that can communicate (e.g., supply) electrical signals via a conductive link electrically connected between the electrodes 156 and the therapy system 158. The control system 160 can control stimulation parameters (e.g., current, voltage, repetition rate, trigger delay, sensing trigger amplitude) for applying electrical stimulation via the electrode(s) 154 to one or more location of the heart 152. The control circuitry 160 can set the stimulation parameters and apply stimulation based on automatic, manual (e.g., user input) or a combination of automatic and manual (e.g., semiautomatic controls. One or more sensors (not shown) can also communicate sensor information to the therapy system 158, which is located external to the patient's body 156. The position of the electrodes 156 relative to the heart can be determined and tracked via an imaging modality, a mapping system 162, direct vision or the like. The location of the electrodes and the therapy parameters thus can be combined to provide corresponding therapy parameter data.

Concurrently with providing a therapy via the therapy system 158, another system or subsystem can be utilized to acquire electrophysiology information for the patient. In the example of FIG. 7, a sensor array 164 includes one or more electrodes that can be utilized for recording patient activity. As one example, the sensor array 164 can correspond to an arrangement of body surface sensors that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, which was filed 10 Nov. 2009, which is incorporated herein by reference. Other arrangements of electrodes can be used, which may be a reduced set of electrodes that does not cover the entire torso and is designed for measuring electrical activity for a particular purpose (e.g., to assist in delivery of therapy).

Alternatively or additionally, in other embodiments, the sensor array 164 can be an invasive sensor, such as an EP catheter having a plurality of electrodes. The EP catheter can be inserted into the patient's body 154 and into the heart for mapping electrical activity for an endocardial surface such as the wall of a heart chamber. As another alternative, the sensor array 164 can be an arrangement of electrodes disposed on other devices, such as patches, which can be placed on or near a patient's heart, endocardially and/or epicardially. These patches can be utilized during open chest and minimally invasive procedures to record electrical activity.

In each of such example approaches for acquiring patient electrical information, including invasively, non-invasively, or a combination of invasive and non-invasive sensors, the sensor array(s) 164 provide the sensed electrical information to a corresponding measurement system 166. The measurement system 166 can include appropriate controls and signal processing circuitry 168 for providing corresponding measurement data 170 that describes electrical activity detected by the sensors in the sensor array 164. The measurement data 170 can include analog or digital information.

The control 168 can also be configured to control the data acquisition process for measuring electrical activity and providing the measurement data 170. The measurement data 170 can be acquired concurrently with the delivering therapy by the therapy system, such as to detect electrical activity of the heart 152 that occurs in response to applying a given therapy (e.g., according to therapy parameters). For instance, appropriate time stamps can be utilized for indexing the temporal relationship between the respective data 170 and therapy parameters to facilitate the evaluation and analysis thereof. The control 168 can also implement a defibrillation mode in which the electrodes are electrically disconnected or otherwise reconfigured to provide a safe environment at which defibrillation can be performed to the patient's body 154 without having to remove the electrodes from the sensor array 164.

Those skilled in the art will appreciate various other approaches that can be employed to obtain the patient measurement data 170. For example, the measurement data 166 can be acquired by myocardial activation imaging in which images of the myocardial activation sequence are obtained by combining measurements obtained by electrocardiographic body surface mapping with three-dimensional anatomical data.

The mapping system 162 is programmed to combine the measurement data 170 corresponding to electrical activity of the heart 152 with patient geometry data 172 by applying an appropriate algorithm to provide corresponding electroanatomical map data 174. The map data 174 can be represent electrical activity of the heart 152, such as corresponding to a plurality of reconstructed electrograms distributed over a cardiac envelope for the patient's heart (e.g., an endocardial or epicardial envelope). As one example, the map data 174 can correspond to electrograms for an epicardial surface of the patient's heart 152, such as based on electrical data that is acquired non-invasively via sensors distributed on the body surface or invasively with sensors distributed on or near the epicardial envelope. Alternatively, the map data 174 can be reconstructed for an endocardial surface of a patient's heart such as a portion of chambers of the patient's heart (e.g., left and right ventricles), such as based on electrical activity that is recorded invasively using an EP catheter or similar devices or recorded non-invasively via body surface sensors. The map data can represent electrical activity for other cardiac envelopes. The particular methods employed by the mapping system 162 for reconstructing the electrogram data can vary depending upon the approach utilized for acquiring the measurement data 170.

In one example, the mapping system 162 generates the map data to represent activation time computed for each of the plurality of points on the surface of the heart from electrograms over a selected cardiac interval (e.g., a selected beat). Since the measurement system 166 can measure electrical activity of the heart concurrently, the resulting electrogram maps and activation maps (e.g., the map data 174) thus can also represent concurrent data for the heart for analysis to quantify an indication of synchrony, as described herein. The interval for which the activation times are computed can be selected based on user input. Additionally or alternatively, the selected intervals can be synchronized with the application of therapy by the therapy system 158.

In the example of FIG. 7, assuming a non-contact type of sensor array 164, the mapping system 162 includes a map generator 176 that constructs electroanatomical map data by combining the measurement data 170 with patient geometry data 172 through an inverse algorithm to reconstruct the electrical activity onto a representation (e.g., a three-dimensional representation) of the patient's organ. The mapping system 162 can also include an electrogram reconstruction engine 178 that processes the electrical activity to produce corresponding electrogram data for each of a plurality of identifiable points on the appropriate cardiac envelope (e.g., an epicardial or endocardial surface) of the patient's heart.

As an example, the geometry data 172 may be in the form of graphical representation of the patient's torso, such as image data acquired for the patient. Such image processing can include extraction and segmentation of anatomical features, including one or more organs and other structures, from a digital image set. Additionally, a location for each of the electrodes in the sensor array 164 can be included in the patient geometry data 172, such as by acquiring the image while the electrodes are disposed on the patient and identifying the electrode locations in a coordinate system through appropriate extraction and segmentation. The resulting segmented image data can be converted into a two-dimensional or three-dimensional graphical representation that includes the region of interest for the patient.

Alternatively, the geometry data 172 can correspond to a mathematical model, such as can be a generic model or a model that has been constructed based on image data for the patient's organ. Appropriate anatomical or other landmarks, including locations for the electrodes in the sensor array 164 can be identified in the geometry data 172 to facilitate registration of the electrical measurement data 170 and performing the inverse method thereon. The identification of such landmarks can be done manually (e.g., by a person via image editing software) or automatically (e.g., via image processing techniques).

By way of further example, the patient geometry data 172 can be acquired using nearly any imaging modality based on which a corresponding representation can be constructed, such as described herein. Such imaging may be performed concurrently with recording the electrical activity that is utilized to generate the patient measurement data 170 or the imaging can be performed separately (e.g., before the measurement data has been acquired).

The system 150 also includes an analysis method 180 that is programmed to assess heart function and provide heart function data 182 based on the map data 174. As described herein, the heart function data 182 can be in the form of an index or indices. Additionally, the analysis system 180 can communicate with the therapy system 158 and the measurement system 166, such as to synchronize and control delivery of therapy and measurement of electrical activity via the sensor array 164. The analysis system 180 can compute a plurality of indices for different therapy parameters (e.g., location and electrical stimulation parameters) based on the map data 174. The analysis method 180 can also compute histogram information (e.g., as shown and described in FIG. 5). The analysis method 180 can also determine a desired (e.g., optimum) set of therapy parameters for achieving desired therapeutic results. The analysis system 180 can also provide an indication of a patient's candidacy for a therapy, which may include one or both of an indication of the patient's expected responsiveness to therapy or expected non-responsiveness to therapy.

In the example, of FIG. 7, the analysis method 180 includes a selection function 184, an exclusion function 186, a synchrony calculator 188 and an optimization component 190. The selection function 184 can be programmed to select an interval of a heart beat for which the analysis and heart function data will be calculated. The selection function 184 can be automated, such as synchronized to application of the therapy via the therapy system. Alternatively, the selection function 184 can be manual or semiautomatic, such as described herein, for selecting one or more cardiac interval.

The exclusion function 186 is programmed to identify and exclude areas from analysis, such as scar areas. The exclusion can be performed based on electrical information, imaging data (e.g., from the patient geometry data 172) or both. The exclusion function 186 can be automatic, based on evaluation of the electrical and/or imaging data, or it can be manual or semiautomatic, such as described herein. Each area (if any) identified for exclusion can be co-registered with the map data, such that the identified areas are not utilized as part of the calculations for assessing heart function. Alternatively, the exclusion can be utilized to remove results.

The synchrony calculator 188 can be programmed to compute one or more indication of synchrony (e.g., in the form of an index) that provides an assessment of heart function as the heart function data. For instance, the synchrony calculator 188 can be programmed to perform one or more of the calculations (e.g., for computing GSI, SSI, ICI and/or late activation index) shown and described here to provide the heart function data 182 accordingly. the synchrony calculator can further compute one or more quantitative indication of synchrony based on conduction data 191, such as disclosed herein with respect to FIG. 2. The conduction data 191 further can be utilized to identify a normal indication of synchrony for a given segment (e.g., anatomical region), such that evaluation of the conduction data relative to the computed synchrony data for a given patient can be used to improve synchrony for the entire heart as well as independently for one or more respective segments that may be determined to be important for mechanical function (e.g., as indicated by a weighting function), as disclosed herein.

The optimization component 190 can be programmed to determine one or more therapy delivery locations (e.g., one or more pacing sites). This may involve positioning one or more electrodes at test sites and evaluating the synchrony determined by the synchrony calculator 188. The electrodes can be implanted at locations based on this evaluation. This can vary depending on, for example, the number and type of electrodes being implanted.

Additionally or alternatively, the optimization component 190 can be utilized to determine one or more therapy parameters, such as post-implantation of the electrodes. The parameterization for programming the implanted device can be based on parameters determined intraoperatively based on quantitative analysis computed by the synchrony calculator 188. For instance, the optimization component 190 can evaluate heart function data (e.g., provided as one or more index) 182 that is computed by the synchrony calculator 188 from map data (e.g., activation map data) 174 acquired in response to therapy applied to the heart during a calibration or programming mode for a plurality of different therapy parameters.

Those skilled in the art will understand appreciate various approaches that can be utilized to vary the location and/or other therapy parameters to achieve a desired therapeutic result. The optimization component 190 can evaluate the therapeutic result, for example, by minimizing the index or indices computed by the index calculator for each set of parameters. The type of location information and therapy parameters further can vary depending on the type of therapy device and the number of electrodes. For example, the therapy system 158 can be implemented to provide for single chamber pacing or multi-chamber pacing as well as may be implemented endocardially or epicardially with respect to the heart 152. As a further example, the optimization can be utilized to adjust parameters for a standard lead configuration or adjust an electric field vector for a lead configuration employing a plurality of ventricular leads.

The heart function data 182 can be utilized to present an indication of heart function on a display 192, which can include text and/or graphics. For instance, the indication of heart function for each set of parameters can be provided as a graphical element that is superimposed onto a cardiac map 194 being visualized on the corresponding display 192. It is to be understood and appreciated that the determination of the heart function data 182 can be performed in real time such that the representation of the heart function on the cardiac map 194 can provide real time guidance and information to facilitate positioning the electrodes 156 within the patient's body 154 as well as setting parameters for delivering therapy to the patient. The therapy parameters can also be provided on the display 192.

By way of further example, the analysis system 180 can employ other measures, such as like percentage of LV that late activated (e.g., from histogram or other data). As an example, the synchrony calculator 188 can be programmed to group the time-based electrical data (e.g., activation or repolarization times for each of the plurality of points into two or more temporally contiguous set of points. For example, points having electrical activity (e.g., a computed activation time or repolarization time) within a corresponding first time period relative to a predetermined time threshold (e.g., an activation time threshold) can be grouped into a first subset of points. Similarly, a temporally contiguous set of points within a corresponding second time period can correspond to a second subset of the points. Thus, the first subset of points can be those having a time before the threshold and the second subset can be those that occur after the threshold. The synchrony calculator 188 can compute an index of late activation based on a relative quantity of the plurality of points are determined to have an activation time or repolarization time that occurs after the computed time threshold (e.g., based on how many points in the second subset versus the first subset). This late activation can be performed intraventricularly (e.g., within the left and/or right ventricles).

Additionally, the late activation can also be computed for each of a plurality of spatial segments into which the heart can be divided, such as anatomical regions or other geometrical regions. For example, the points can be grouped into segments according to each segments relative contribution to mechanical function of the heart. Relative segmental weighting can be applied to such segments to evaluate relative synchrony among the segments as they pertain to heart function. Additionally, the analysis system 180 can further determine how percentage of activation of a chamber changes intraoperatively, such as in response to applying different types or therapies or different therapy (e.g., pacing) modes.

As a further example, the late activation time can be computed for a plurality of different conditions (e.g., without CRT, and with CRT applied at different locations and with different parameters) to provide corresponding indications of synchrony. The computed late activation time for each condition can be compared (e.g., manually or by the analysis system 180 automatically) to help evaluate patient responsiveness to CRT as well as to determine CRT parameters as disclosed herein.

In addition to the dyssynchrony computations described above, the analysis system 180 may be configured to assess synchrony according to one or more of the following other calculations:
   a. QRS onset (or end of pacing spike) to beginning of ventricular activation. For instance, the analysis system 180 can determine an earliest LV activation from the map data (e.g., on isochrones) and subtract the beginning of QRS.
   b. LV activation time from beginning to end: latest LV activation time–earliest LV activation time.
   c. LV delay estimation: the analysis system 180 can estimate LV delay for the entire LV free wall area by dividing LV free wall into segments and then calculate the size. Then estimate area size. As one example, area size=x % (example) of the total area. And the time of the last area is Time to x % LV free wall activation. This can be to any percentage of the LV.
   d. Locate the % of LV region that has an activation time that occurs some predetermined percentage greater than (e.g., >50%) of QRS duration. For example, if a patient has a QRS width of 120 ms, the analysis system 180 can compute the percentage of the ventricle that activates in the last 20 ms (e.g., how much activation occurs later than the normal 100 ms). The time threshold can be programmable and can be set in response to a user input.

The analysis thus can employ thresholds (e.g., corresponding to normal values of synchrony, plus two standard deviations) for these and other quantitative indications of synchrony disclosed herein to ascertain whether the results of such analysis indicates dyssynchrony as well as the degree of such dyssynchrony.

FIG. 8A through FIG. 14 depict examples of electrocardiographic maps that can be generated to represent quantitative analysis of synchrony based on systems and methods disclosed herein (e.g., the analysis system 20 of FIG. 1 or analysis method 180 of FIG. 7, respectively).

Figures 8A, 8B:
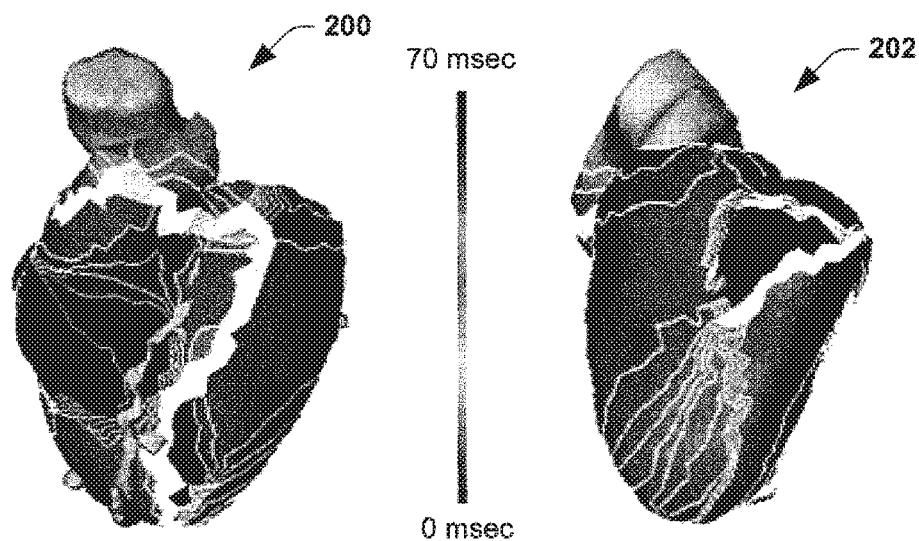
FIGS. 8A and 8B depict examples of electrocardiographic maps for a baseline patient condition.

FIGS. 8A and 8B depict examples of electrocardiographic maps 200 and 202, including a left-anterior-oblique (LAO) view in FIG. 8A and a lateral view in FIG. 8B. The maps 200 and 202 in FIGS. 8A and 8B, respectively, depict activation maps showing interventricuar dyssynchrony for a baseline patient condition.

Figures 9A, 9B:
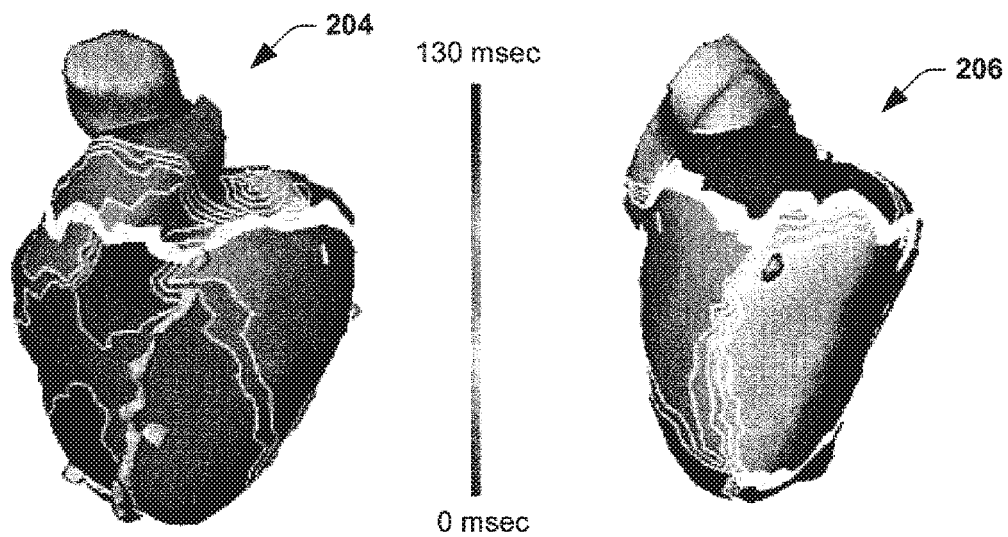
FIGS. 9A and 9B depict examples of electrocardiographic maps demonstrating a response to delivery of a therapy for the same patient as in FIGS. 8A and 8B.

FIGS. 9A and 9B depict examples of electrocardiographic maps 204 and 206 demonstrating a response to delivery of a therapy (e.g., CRT) for the same patient as in FIGS. 8A and 8B. A comparison between the maps 200 and 202 relative to the maps 204 and 206 demonstrates a significant improvement in response to delivery of the therapy. Thus, the comparative analysis can confirm that the patient is a responder to CRT.

Figure 10A:
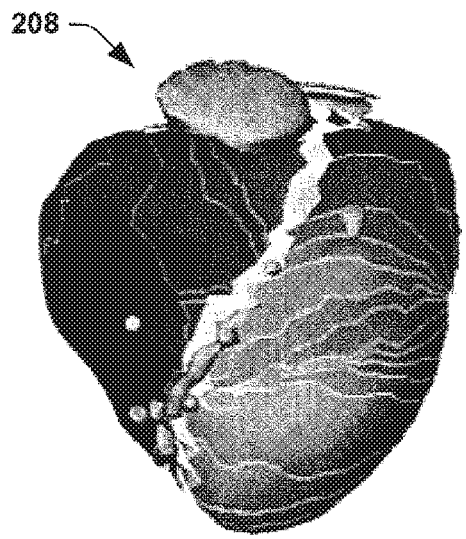
FIGS. 10A and 10B depict examples of electrocardiographic maps for a baseline patient condition.
Figure 10B:
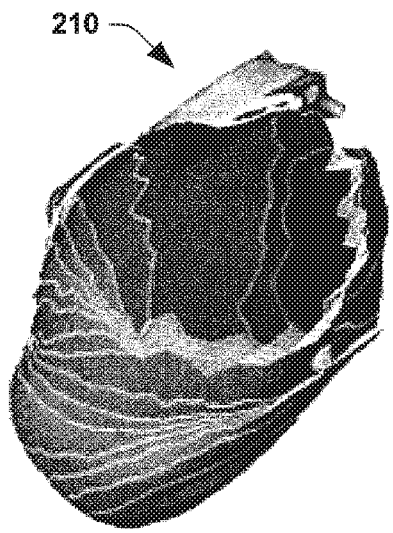
Figure 11A:
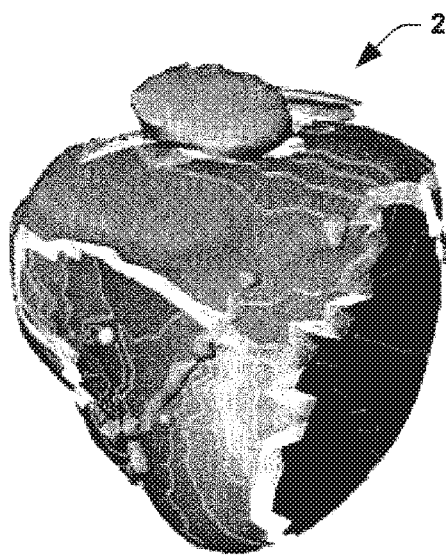
FIGS. 11A and 11B depict examples of electrocardiographic maps demonstrating a patient response to delivery of a therapy for the same patient as FIGS. 10A and 10B.
Figure 11B:

FIGS. 10A and 10B depict examples of electrocardiographic maps 208 and 210 demonstrating a baseline condition for another patient. In the maps 208 and 210, interventricular dyssynchrony is apparent as evidenced by the much later activation time in the left ventricle than the right ventricle. FIGS. 11A and 11B depict examples of electrocardiographic maps 212 and 214 demonstrating a patient response to delivery of a therapy for the same patient as in the example of FIGS. 10A and 10B. In the maps 212 and 214, the pacing results in increased late activation relative to the baseline maps 208 and 210 of FIGS. 10A and 10B. In this example, the increased late activation in the left ventricle can be utilized to confirm that the patient is a non-responder to the particular CRT. This can be used to select an alternative form or therapy or surgery.

Figure 12:
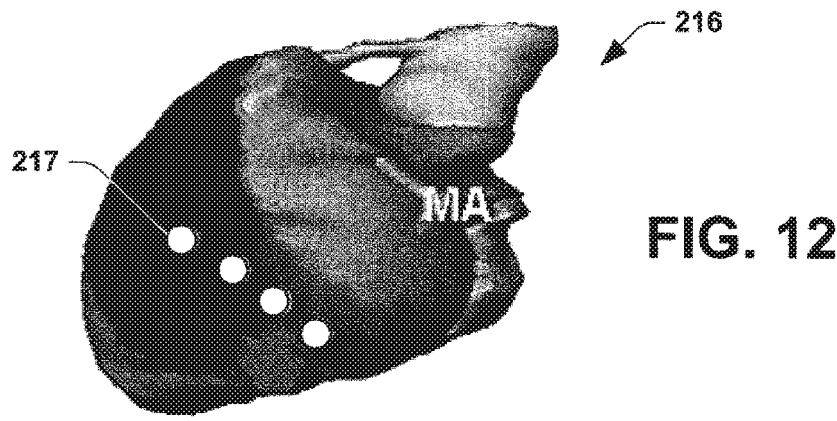
FIGS. 12, 13 and 14 depict examples of electrocardiographic maps demonstrating patient responses for delivery of therapy at different locations and with different therapy parameters.
Figure 13:
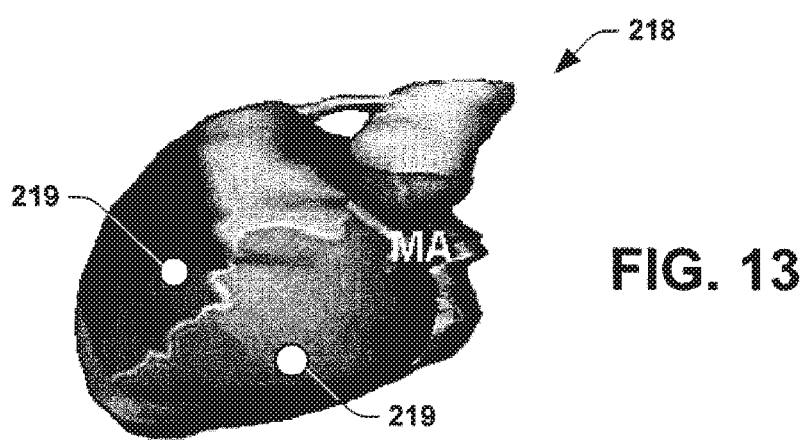
Figure 14:
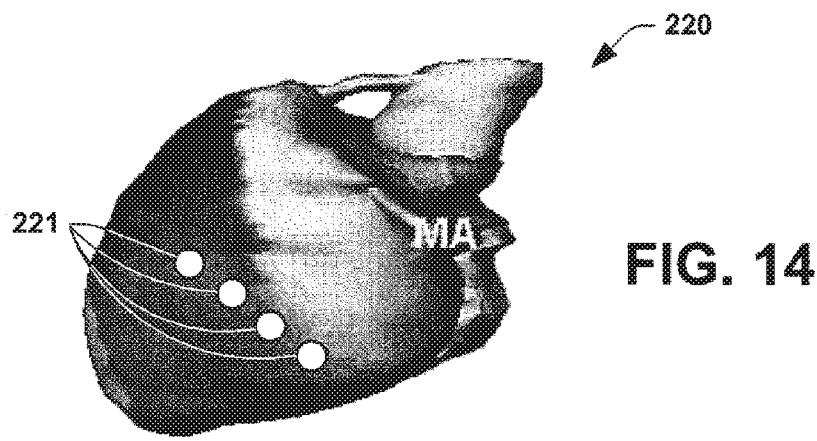

FIGS. 12, 13 and 14 depict examples of electrocardiographic maps 216, 218 and 220 demonstrating responses for a given patient to delivery of therapy, such as at different locations and with different therapy parameters (e.g., similar to the map 194 that can be output in the example of FIG. 7). These maps 216, 218 and 220 or similar maps to help determine lead placement and optimal pacing parameters, which can be utilized as tools during CRT and/or after CRT device implant.

In FIG. 12, the map 216 depicts an example of pacing in which one of four available leads (e.g., lead 217) is activated to supply an electric field for providing CRT. In FIG. 13, the map 218 depicts an example of bi-ventricular pacing in which a pair of leads (e.g., leads 219) are activated to supply an electric field for providing CRT. While the map 218 demonstrates an improved response relative to the example of FIG. 12, there remains a late activation region in posterolateral LV causing poor electrical synchrony and a corresponding poor hemodynamic response to such pacing. FIG. 14 depicts an example map 220 in which four available leads (e.g., leads 221) is activated to provide pacing for CRT. The map 220 demonstrates significantly improved electrical synchrony relative to the approaches in FIGS. 12 and 13 as to support good hemodynamic response to such pacing.

Figure 15:
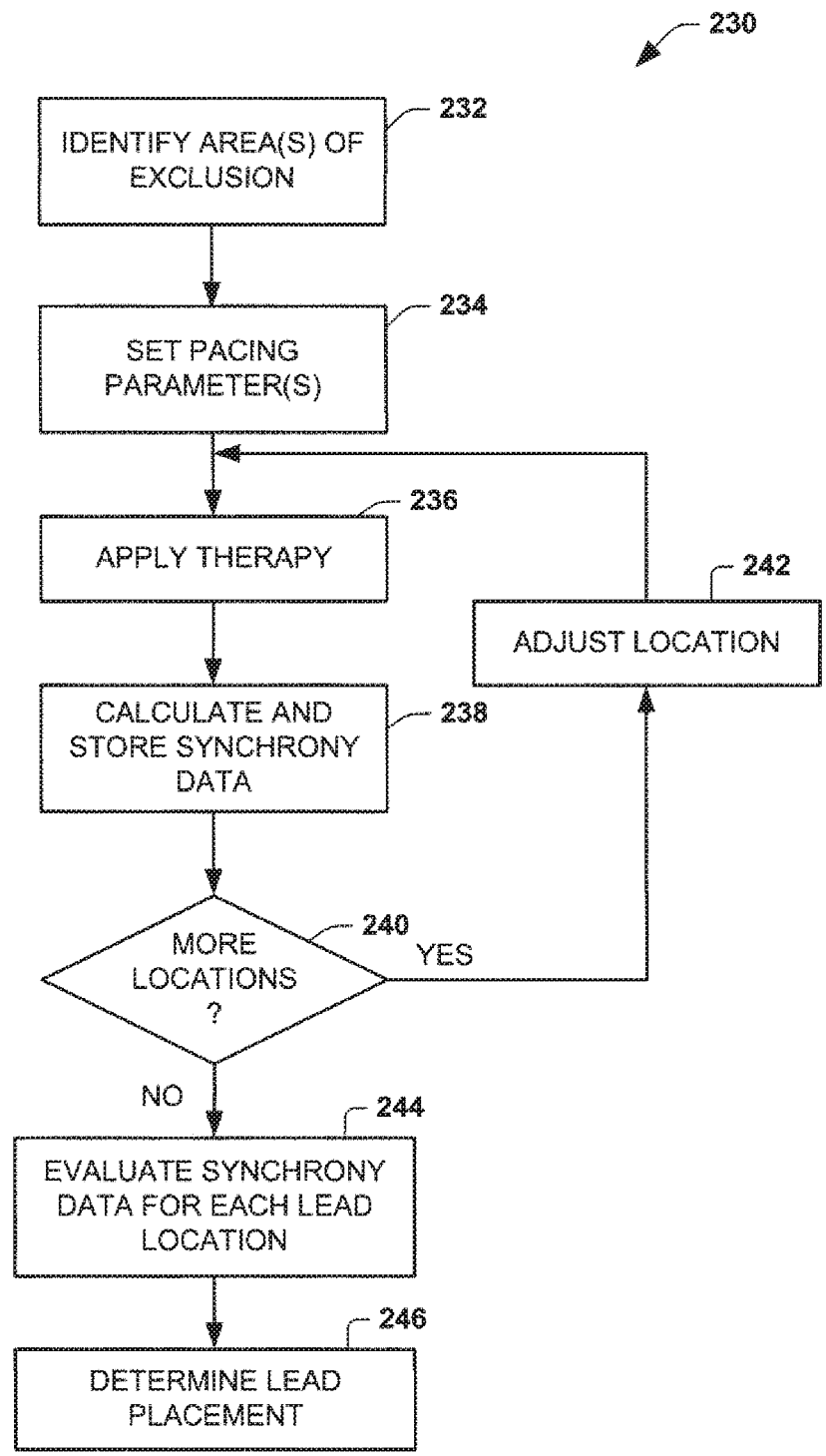
FIG. 15 is a flow diagram illustrating an example of a method to determine a location for delivery of a therapy.

FIG. 15 is flow diagram depicting an example of a method 230 that can be utilized to facilitate lead placement for delivery of a therapy based upon one or more quantified indication of synchrony, such as shown and described herein. The method 230 can be implemented in the context of the system of FIG. 7, for example, as computer executable instructions corresponding to the analysis method 180 of FIG. 7.

The method begins at 232 in which areas are identified and excluded from further assessment in the method of 230. The areas can be identified as corresponding to scar areas or areas otherwise having conduction or low voltage electrograms that are below a corresponding threshold. The identification can be performed automatically (e.g., via thresholding) or based on user selection of areas such as can be performed based on analysis of imaging data such as described herein.

At 234, pacing parameters are set. The parameters can include a variety of electrical stimulation parameters, which further can vary depending on the number of electrodes. Examples of parameters that can be utilized in the systems and methods disclosed herein include, current, voltage, repetition rate, trigger delay and sensing trigger amplitude. The parameters can also include a delay between pacing times for different electrodes, such as an atrio-ventricular delay (e.g., for leads in atrium and ventricle) as well as ventricular-ventricular delays (e.g., for leads in the respective ventricles). Parameters can also be set to establish an electrical field vector by controlling stimulation parameters for different electrodes.

At 236, a therapy can be delivered at a location based on the initial parameters at 234. The therapy can include electrical stimulation, but is not limited to electrical stimulation. For instance, the therapy can include electrical pacing stimulation that is applied via a pacing electrode or electrodes that have been inserted and are in contact with one or more corresponding locations of the heart. The location of the electrodes can be determined from electrical information obtained by the mapping system (system 162 of FIG. 7), based on imaging data (stored with the patient geometry data 172 of FIG. 6), such as via x-ray (e.g., chest-xray or fluoroscopy), ultrasound or other known imaging modalities that can be performed in conjunction with pacing.

At 238, one or more indication of synchrony can be calculated and stored in memory as synchrony data. The synchrony data can include any one or more of the indices disclosed herein, for example. At 240, a determination is made as to whether additional pacing locations exist for which indices can be calculated as part of the method 230. Different pacing parameters can also be adjusted for each location, if desired, such as can be implemented according to the method of FIG. 16 as an inner loop within the method 230 between 238 and 240. If one or more additional locations exist for discovering lead placement, the method proceeds to 242 in which the location is changed accordingly. Each location can be entered manually by the user or it can be determined by analysis performed by the mapping system (e.g., mapping system 162 of FIG. 7).

From 242, the method returns to 236 in which a corresponding therapy is applied at the next location. In conjunction with application of the therapy, an interval can be selected associated with the therapy that is being applied and corresponding time-based electrical characteristics can be calculated as shown and described herein. Based upon the calculated time-based electrical characteristics, at 238, the corresponding index can be calculated and stored in memory.

Once the potential set of pacing locations have been exhausted or the testing is otherwise terminated, the method proceeds to 244 in which the synchrony data for each location can be evaluated. Based on the evaluation of synchrony data (e.g., a minimization thereof), a desired location for delivery of therapy (e.g., lead placement) can be determined at 246. It will be understood and appreciated that the evaluation at 244 can be performed within the loop from 236 through 242, alternatively. Additionally, the results of the index calculations can be utilized to help guide adjustments at 242 to facilitate determining one or more appropriate locations that can be utilized for delivering the desired therapy.

Figure 16:
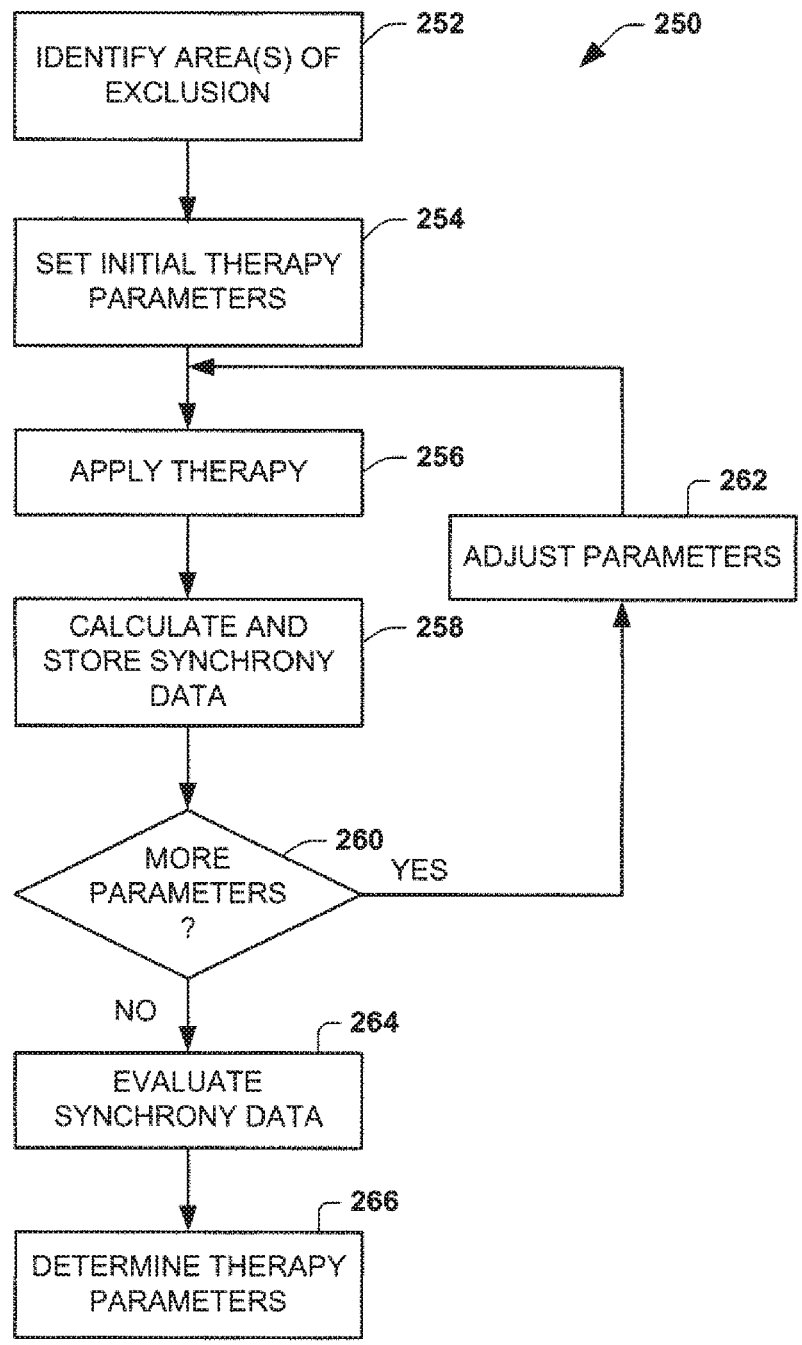
FIG. 16 is a flow diagram illustrating an example of a method to determine parameters for delivery of a therapy.

FIG. 16 is flow diagram depicting an example of a method 250 that can be utilized for optimizing delivery of a therapy based upon a calculating an index, such as shown and described herein. The method 250 can be implemented in the context of the system 150 of FIG. 7, for example, as computer executable instructions corresponding to the analysis method 180 of FIG. 7.

The method begins at 252 in which areas are identified and excluded from further assessment in the method of 250. The areas can be identified as corresponding to scar areas or areas otherwise having conduction or low voltage electrograms that are below a corresponding threshold. The identification can be performed automatically (e.g., via thresholding) or based on user selection of areas such as can be performed based on analysis of imaging data such as described herein. A corresponding interval of a beat can also be selected. The interval selection can occur in response to a user input or automatically based upon evaluation of acquired electrical data that has been acquired in real time, as disclosed herein.

At 254, initial therapy parameters can be set. As described herein, the parameters can include electrical stimulation parameters, such as amplitude, phase, duration and a relative delay between activation at different lead locations. The parameters can also include locations for one or more leads at which stimulation is applied. At 256, a therapy can be delivered at a location based on the initial parameters at 254. The therapy can include an electrical stimulation, but is not limited to electrical stimulation. For instance, the therapy can include electrical pacing stimulation that is applied via a pacing electrode or electrodes that have been inserted and are in contact with one or more corresponding locations of the heart. The location of the electrodes can be determined from electrical information obtained by the mapping system (system 162 of FIG. 7), based on imaging data (stored with the patient geometry data 172 of FIG. 7), such as via x-ray (e.g., chest-xray or fluoroscopy), ultrasound or other known imaging modalities that can be performed in conjunction with pacing.

At 258, one or more index can be calculated and stored in memory. The index can include any one or more of the indices disclosed herein. At 260, a determination is made as to whether any additional parameters exist for which indices can be calculated as part of the method 250. As mentioned above, the parameters can include location, amplitude, phase, frequency or the like. The particular parameters for a given pacing electrode structure can vary according to the particular pacing electrode or combination of electrodes that are being utilized for implementing such pacing. If additional parameters exists for which indices are to be calculated, the method proceeds to 262 in which parameter adjustments are made. The parameter adjustments at 260 can include moving to a different location, changing an electrode stimulation parameter or a combination thereof. The adjustments can be automated in response to a control signal or manual based on information that can be presented to the user.

From 262, the method returns to 256 in which a corresponding therapy is applied at the location for the next therapy parameters. In conjunction with application of the therapy, an interval is selected associated with the therapy that is being applied and corresponding activation data can be calculated as shown and described herein. Based upon the calculated activation data, at 258, the corresponding index can be calculated and stored in memory.

Once available set of parameters have been exhausted or the testing is otherwise terminated, the method proceeds to 264 in which the index data can be evaluated to determine a desired set of parameters. Based on the evaluation of index data (e.g., a minimization thereof), a set of therapy parameters can be determined at 266. It will be understood and appreciated that the evaluation at 264 can be performed within the loop from 254 through 262, alternatively. Additionally, the results of the index calculations can be utilized to help guide stimulation parameter adjustments at 260 to facilitate determining an appropriate set of parameters that can be utilized for delivering the desired therapy.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 17. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 17:
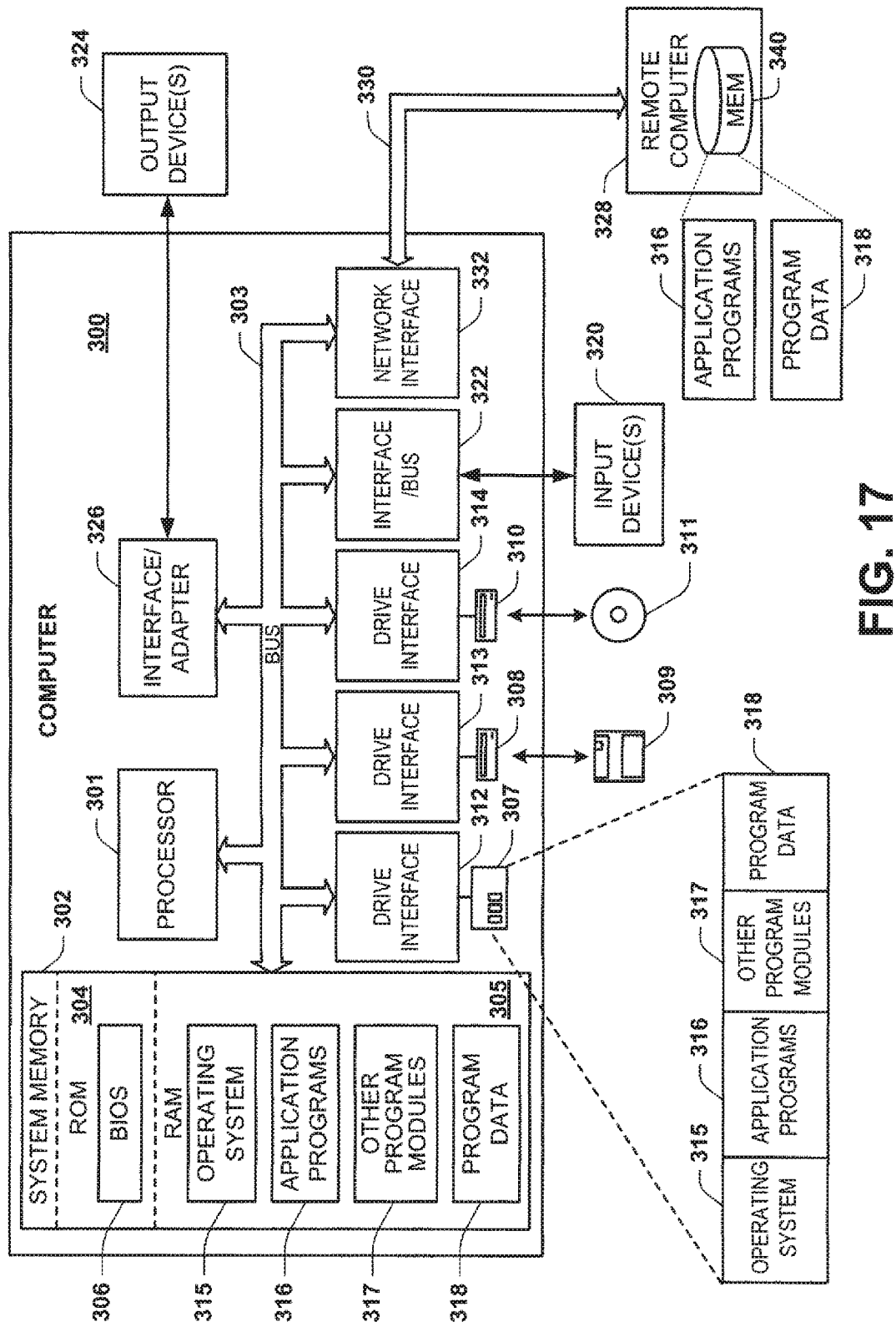
FIG. 17 depicts an example computing environment that can be used to perform methods according to an embodiment of the invention.

In this regard, FIG. 17 illustrates one example of a computer system 300 that can be employed to execute one or more embodiments of the invention, such as including acquisition and processing of sensor data, processing of image data, as well as analysis of transformed sensor data and image data associated with the analysis of cardiac electrical activity. Computer system 300 can be implemented on one or more general purpose networked computer systems, embedded computer systems, routers, switches, server devices, client devices, various intermediate devices/nodes or stand alone computer systems. Additionally, computer system 300 can be implemented on various mobile clients such as, for example, a personal digital assistant (PDA), laptop computer, pager, and the like, provided it includes sufficient processing capabilities to perform the functions disclosed herein.

Computer system 300 includes processing unit 301, system memory 302, and system bus 303 that couples various system components, including the system memory, to processing unit 301. Dual microprocessors and other multi-processor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the present invention.

A number of program modules may be stored in drives and RAM 305, including operating system 315, one or more application programs 316, other program modules 317, and program data 318. The application programs and program data can include functions and methods programmed to acquire, process and display electrical data from one or more sensors, such as shown and described herein. The application programs and program data can include functions and methods programmed to process data acquired for a patient for assessing heart function and/or for determining parameters for delivering a therapy, such as shown and described herein with respect to FIGS. 1-16.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples and embodiments of the invention. It is, of course, not possible to describe every conceivable combination of components or methodologies for purposes of describing the invention, but one of ordinary skill in the art will recognize that many further combinations and permutations of the present invention are possible. Accordingly, the invention is intended to embrace all such alterations, modifications and variations that fall within the scope of the appended claims. In the claims, unless otherwise indicated, the article "a" is to refer to "one or more than one."

What is claimed is:

1. A system, comprising:
a computing device configured to store data and execute machine readable instructions, the data including electrical data representing measurements of cardiac electrophysiological activity for a plurality of points across at least one spatial region of a surface of a heart of a patient, the electrical data being reconstructed for the at least one spatial region of the heart that includes the plurality of points based on cardiac signals measured non-invasively and concurrently via sensors distributed across an outer surface of a body of the patient, the instructions to compute at least one indication of synchrony based on an analysis of the electrical data for the at least one spatial region of the surface of the heart, the at least one indication of synchrony providing a quantitative assessment of at least one of a heart electrical function, a heart mechanical function or a hemodynamic performance, wherein the instructions of the computing device are further configured to determine a treatment location based on the at least one indication of synchrony, the treatment location being determined based on the measurements of cardiac electrophysiological activity.

2. The system of claim 1, wherein the the measurements of cardiac electrophysiological activity are acquired intraoperatively to provide spatial guidance to identify one or more sites for delivering a therapy to the patient.

3. The system of claim 1, further comprising a therapy system to deliver a therapy based on at least one therapy parameter, the at least one therapy parameter being computed based on the at least one indication of synchrony, the computing device being configured to adjust the at least one therapy parameter in response to feedback corresponding to updated measurements of cardiac electrophysiological activity.

4. The system of claim 1, wherein the instructions of the computing device are further configured to determine at least one therapy parameter for a therapy based on the at least one indication of synchrony, the at least one therapy parameter comprising at least one of a quantity of the therapy, a duration of the therapy and a time between delivery of consecutive therapies.

5. The system of claim 1, wherein the plurality of points across the at least one spatial region of the surface of the heart of the patient are divided into a plurality of spatial regions, each spatial region comprising some of the plurality of points, the instructions are further configured to compute a respective indication of synchrony for each of the plurality of spatial regions and to quantify synchrony for the heart based on a comparison of the respective indication of synchrony computed for each of the plurality of spatial regions.

6. The system of claim 1, wherein the instructions are further configured to:
compute time-based electrical characteristics for the plurality of points based on the measurements of cardiac electrophysiological activity during at least one time interval;
calculate a standard deviation values for a plurality of spatial segments distributed across the at least one spatial region of the heart based on the computed time-based electrical characteristics of the plurality of points within each respective segment; and
identify at least one of the plurality spatial segments having an increased dispersion for the time-based electrical characteristics relative to other spatial segments of the plurality of spatial segments based on the calculated standard deviation values.

7. The system of claim 6, further comprising a therapy system to deliver a therapy to the heart based on at least one therapy parameter to decrease the dispersion for the time-based electrical characteristics in the at least one identified spatial segment relative to the other spatial segments, the at least one therapy parameter being computed based on the at least one indication of synchrony.

8. The system of claim 1, wherein the instructions of the computing device are further configured to:
compute the at least one indication of synchrony based on the electrical data that is acquired non-invasively via the sensors distributed on the outer surface of the body of the patient and other electrical data acquired invasively via one or more sensors within the body of the patient; and generate map data to display the at least one indication of synchrony.

9. The system of claim 1, wherein the instructions of the computing device are further configured to:
identify at least one area of the heart that does not contribute to mechanical function; and
exclude the identified at least one area from the at least one spatial region of the heart, such that the electrical data for points residing in each excluded area are not used in computing the at least one indication of synchrony.

10. The system of claim 9, wherein the instructions of the computing device are further configured to:
determine at least one therapy parameter based on the at least one indication of synchrony; and
cause a therapy system to deliver a therapy based on the at least one therapy parameter.

11. The system of claim 10, further comprising the therapy system, wherein the computing device is configured to control the therapy system based on the at least one therapy parameter and to adjust the at least one therapy parameter in response to changes in the at least one indication of synchrony computed from updated cardiac signals acquired from the patient.

12. The system of claim 11, wherein the instructions of the computing device are further configured to:
compute the at least one indication of synchrony based on the electrical data that is acquired non-invasively via the sensors distributed on the outer surface of the body of the patient and invasively via one or more other sensors within the body of the patient; and
generate map data to display the at least one indication of synchrony.

13. A system, comprising:
a computing device configured to store data and execute machine readable instructions, the data including electrical data representing measurements of cardiac electrophysiological activity for a plurality of points across at least one spatial region of a surface of a heart of a patient, the electrical data being reconstructed for the at least one spatial region of the heart that includes the plurality of points based on cardiac signals measured non-invasively and concurrently via sensors distributed across an outer surface of a body of the patient,
wherein the plurality of points across the at least one spatial region of the surface of the heart of the patient are divided into a plurality of spatial regions, each spatial region comprising some of the plurality of points, and
wherein the instructions are further configured to compute at least one indication of synchrony based on an analysis of the electrical data to provide an assessment of mechanical synchrony of the heart based on electrical measurements by weighting each of the plurality of spatial regions according to a respective contribution to the heart mechanical function and/or the hemodynamic performance.

14. A system, comprising:
a computing device configured to store data and execute machine readable instructions, the data including electrical data representing measurements of cardiac electrophysiological activity for a plurality of points across at least one spatial region of a surface of a heart of a patient, the electrical data being reconstructed for the at least one spatial region of the heart that includes the plurality of points based on cardiac signals measured non-invasively and concurrently via sensors distributed across an outer surface of a body of the patient, the instructions to at least:
identify at least one area of the heart of the patient that does not contribute to a mechanical function;
exclude the at least one identified area from the at least one spatial region of the heart, such that the electrical data for points residing in each excluded area are not used in computing at least one indication of synchrony; and
compute the at least one indication of synchrony based on analysis of the electrical data for the at least one spatial region of the surface of the heart, the at least one indication of synchrony providing a quantitative assessment of at least one of a heart electrical function, a heart mechanical function or a hemodynamic performance.

15. The system of claim 14, wherein the instructions of the computing device are further configured to:
determine at least one therapy parameter based on the at least one indication of synchrony; and
cause a therapy system to deliver a therapy based on the at least one therapy parameter.

16. The system of claim 15, further comprising the therapy system, wherein the computing device is configured to control the therapy system based on the at least one therapy parameter and to adjust the at least one therapy parameter in response to changes in the at least one indication of synchrony computed from updated cardiac signals acquired from the patient.

17. The system of claim 16, wherein the instructions of the computing device are further configured to:
compute the at least one indication of synchrony based on the electrical data that is acquired non-invasively via the sensors distributed on the outer surface of the body of the patient and invasively via one or more sensors within the body of the patient; and
generate map data to display the at least one indication of synchrony.

18. The system of claim 15, wherein the instructions of the computing device are further configured to determine a treatment location based on the at least one indication of synchrony, the treatment location being determined based on the measurements of cardiac electrophysiological activity acquired intraoperatively to provide spatial guidance to identify one or more sites for delivering a therapy.

19. The system of claim 15, wherein the plurality of points across the surface of the heart is divided into a plurality of spatial regions, each spatial region comprising some of the plurality of points, the instructions are further configured to compute a respective indication of synchrony for each of the plurality of spatial regions and to quantify synchrony for the heart based on a comparison of the indication of synchrony computed for each of the plurality of spatial regions.

20. A system, comprising:
a computing device configured to store data and execute machine readable instructions, the data including electrical data representing measurements of cardiac electrophysiological activity for a plurality of points across at least one spatial region of a surface of a heart of a patient, the electrical data being reconstructed for the at least one spatial region of the heart that includes the plurality of points based on cardiac signals measured non-invasively and concurrently via sensors distributed across an outer surface of a body of the patient, the instructions to at least:

identify at least one area of the heart of the patient that does not contribute to a mechanical function;

exclude the at least one identified area from the at least one spatial region of the heart, such that the electrical data for points residing in each excluded area are not used in computing at least one indication of synchrony; and compute the at least one indication of synchrony based on analysis of the electrical data for the at least one spatial region of the surface of the heart, the at least one indication of synchrony providing a quantitative assessment of at least one of a heart electrical function, a heart mechanical function or a hemodynamic performance;

compute time-based electrical characteristics for the plurality of points based on the measurements of cardiac electrophysiological activity during at least one time interval;

calculate a standard deviation values for a plurality of spatial segments distributed across the at least one spatial region of the heart based on the computed time-based electrical characteristics of the plurality of points within each respective segment;

identify at least one of the plurality spatial segments having an increased dispersion for the time-based electrical characteristics relative to other spatial segments of the plurality of spatial segments based on the calculated standard deviation values;

determine at least one therapy parameter based on the at least one indication of synchrony; and cause a therapy system to deliver a therapy based on the at least one therapy parameter, wherein the therapy system is configured to deliver the therapy to the heart based on the at least one therapy parameter to decrease the dispersion for the time-based electrical characteristics in the at least one identified spatial segment relative to the other spatial segments.

\* \* \* \* \*